(12) United States Patent
Cash et al.

(10) Patent No.: US 9,753,031 B2
(45) Date of Patent: Sep. 5, 2017

(54) APTAMER COATED MEASUREMENT AND REFERENCE ELECTRODES AND METHODS USING SAME FOR BIOMARKER DETECTION

(75) Inventors: Stephen Lee Cash, Yorkshire (GB); Keith Robson, Durham (GB); Ian Anthony Kinloch, Lancashire (GB); Peter George Stockley, Yorkshire (GB)

(73) Assignee: Sapient Sensors Limited (GB)

( * ) Notice: Subject to any disclaimer, the term of this patent is extended or adjusted under 35 U.S.C. 154(b) by 807 days.

(21) Appl. No.: 14/008,622

(22) PCT Filed: Apr. 2, 2012

(86) PCT No.: PCT/GB2012/050745
§ 371 (c)(1),
(2), (4) Date: Dec. 19, 2013

(87) PCT Pub. No.: WO2012/131403
PCT Pub. Date: Oct. 4, 2012

(65) Prior Publication Data
US 2014/0162893 A1   Jun. 12, 2014

(30) Foreign Application Priority Data
Mar. 31, 2011   (GB) .................. 1105481.4

(51) Int. Cl.
*G01N 27/416*   (2006.01)
*G01N 33/543*   (2006.01)
*C12M 1/34*   (2006.01)
*C12Q 1/68*   (2006.01)

(52) U.S. Cl.
CPC .................. *G01N 33/5438* (2013.01)

(58) Field of Classification Search
USPC ....... 422/69; 435/7.4, 287.2, 6.1, 6.11, 6.12, 435/91.1, 91.31; 436/501; 506/9, 16; 536/23.1
See application file for complete search history.

(56) References Cited

U.S. PATENT DOCUMENTS

| | | |
|---|---|---|
| 4,713,165 A | 12/1987 | Conover et al. |
| 7,854,826 B2 | 12/2010 | So et al. |
| 2004/0106190 A1 | 6/2004 | Yang et al. |
| 2005/0112617 A1* | 5/2005 | Diessel ................ C12Q 1/6816 435/6.11 |
| 2005/0136529 A1 | 6/2005 | Yang et al. |
| 2005/0229334 A1* | 10/2005 | Huang .................... A61K 8/02 8/405 |
| 2008/0262740 A1 | 10/2008 | Potter |
| 2010/0133510 A1 | 6/2010 | Kim et al. |

FOREIGN PATENT DOCUMENTS

| | | |
|---|---|---|
| EP | 0121385 A1 | 10/1984 |
| EP | 1619496 | 1/2006 |
| EP | 1645871 | 4/2006 |
| JP | 2004-347532 A | 12/2004 |
| JP | 2006-030132 | 2/2006 |
| JP | 2009-509175 A | 3/2009 |
| JP | 2009-264904 | 11/2009 |
| JP | 2010-127931 A | 6/2010 |
| WO | 03/087798 | 4/2003 |
| WO | 2004113910 A1 | 12/2004 |
| WO | 2007/001401 | 1/2007 |
| WO | WO 2007/001401 * | 1/2007 |
| WO | 2007102629 A1 | 9/2007 |
| WO | WO 2007/102629 * | 9/2007 |
| WO | 2008/048222 A2 | 4/2008 |
| WO | WO 2008/048222 * | 4/2008 |
| WO | 2012131403 A4 | 10/2012 |

OTHER PUBLICATIONS

Yang et al, Electroanalysis, vol. 23, No. 4, pp. 1007-1012 (2011).*
H. Karasawa, F.Iwata, H. Nakao, H, Hayashi, K. Hirano, S.Sugiyama, T.Ohtani and A. Sasaki, 'Nanometer-scale observation of metalized-DNA nanowires using a scanning near-field optical microscopy', 2005 Nendo Seimitsu Kogakkai Shuki Taikai Gakujyutsu Koenkai Koen Ronbunshu [Proceedings of the 2005 JSPE Autumn Meeting], Sep. 1, 2005, p. 767-768.
Kuan-I-Chen, et al., "Silicon nanowire field-effect transistor-based biosensors for biomedical diagnosis and cellular recording investigation," Nano Today (2011) vol. 6, pp. 131-154.
Kocalka, P., A.H. El-Sagheer, and T. Brown, 'Rapid and efficient DNA strand cross-linking by click chemistry', Chembiochem., 2008. 9(8): p. 1280-5.
El-Sagheer, A.H. and T. Brown, 'Click chemistry with DNA', Chem. Soc. Rev., 2010. 39: p. 1388-1405.
Someya, A. et al., 'Alcohol Vapour Sensors Based on Single-Walled Carbon Nanotube Field Effect Transistors', Nano Letters, vol. 3, No. 7, 877-881.
Suehiro, J. et al., 'Fabrication of Carbon Nanotube-based Gas Sensor Using Dielectrophoresis and its application for ammonia detection by impedance spectroscopy', Journal of Physics D: Applied Physics, vol. 36 (2003), L109-L114.

(Continued)

*Primary Examiner* — Jane Zara
(74) *Attorney, Agent, or Firm* — Jansson Munger; McKinley & Kirby Ltd.

(57) ABSTRACT

A device for identifying the presence of a specific target molecule or biomarker by the detection of a change in an electrical property includes a measurement sensor 8 comprising a semiconducting sensor structure 12 capable of conjugating with the biomarker, thus giving rise to the said change in electrical property, and an electrode system 3, 4 for conducting a signal from the device. According to the invention there is a further such sensor 9, of substantially identical form but having its sensor structure 14 already conjugated with the biomarker, or otherwise capped, e.g. using a further oligonucleotide strand, so as to act as an internal reference. When a biological sample, e.g. saliva, is applied to the electrodes, the reference enables the discounting of all environmental effects other than the biomarker. The invention provides a simple, cheap and accurate text for one or more biomarkers that can be used in the field without complex equipment.

27 Claims, 15 Drawing Sheets

(56) References Cited

OTHER PUBLICATIONS

Vijayaraghavan, A. et al, 'Ultra-Large-Scale Directed Assembly of Single-Walled Carbon Nanotube Devices', Nano Letters, vol. 7, No. 6, 1556-1560.
Tey, J. N. et al, 'Direct Detection of Herion Metabolites Using a Competitive Immunoassay Based on a Carbon-Nanotube Liqud-Gated Field-Effect Transistor', Small (2010), vol. 6, No. 9, 993-998.
Jennifer Chu, A One-Hour Cancer Detector, MIT Technology Review, Mar. 1, 2011 (http://www.technologyreview.com/biomedicine/32443/?nliid=4181).
Haun, B. et al., "Micro-NMR for Rapid Molecular Analysis of Human Tumor Samples", Sci Transl Med, Feb. 23, 2011, vol. 3, Issue 71.
International Search Report and Written Opinion, PCT/GB2012/050745,Sapient Sensors Limited, Aug. 7, 2012.
United Kingdom Search Report, GB1105481.4, Sapient Sensors Limited, Jul. 27, 2011.
L. Yang et al. "Electrochemiluminescence apatmer biosensor for detection of Thrombin based on CdS QDs/ACNTs electrode", Electroanalysis, vol. 23, pp. 1007-1012. Date: 2011.
Y Yuan et al. "A signal-on electrochemical probe-label-free aptasensor using gold-platinum alloy and stearic acide as enhancers", Biosensors & Bioelectronics, vol. 26, pp. 881-885. Date: 2010.
Y Li et al. "Nanomaterial-amplified "signal off/on" electrogenerated chemiluminescence aptasensors for the detection of thrombin", Biosensors & Bioelectronics, vol. 26, pp. 754-759. Date: 2010.
Japanese Office Action, Serial No. 2014-501728, Publication No. 2014-518567, Sapient Sensors Limited, Nov. 15, 2016.

\* cited by examiner

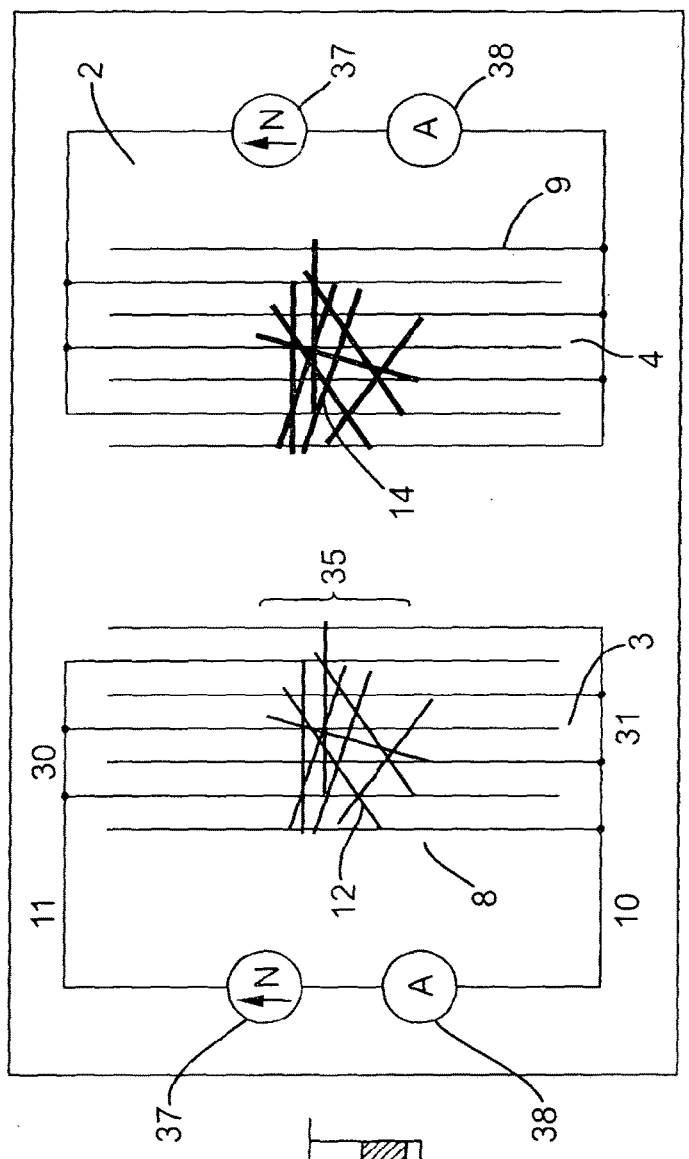
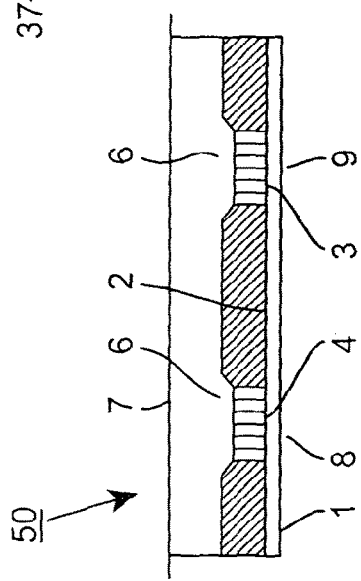
Figure 2
Figure 1

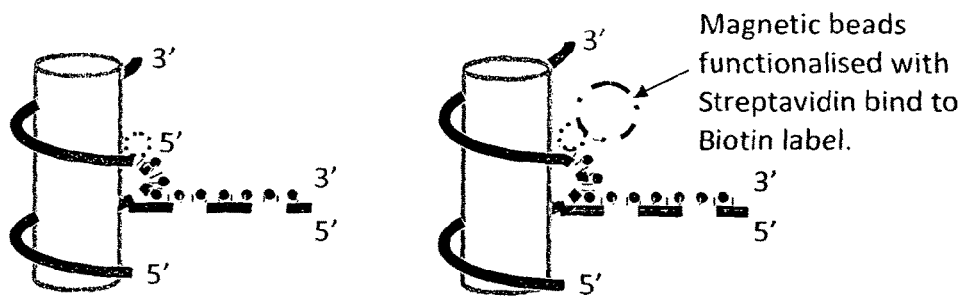
Figure 7(c)
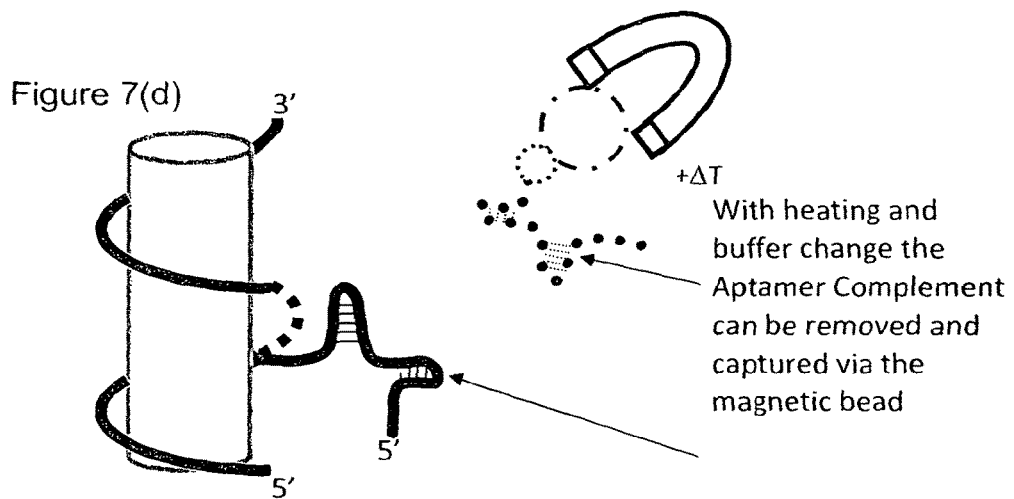
Figure 7(d)
Figure 7(e)
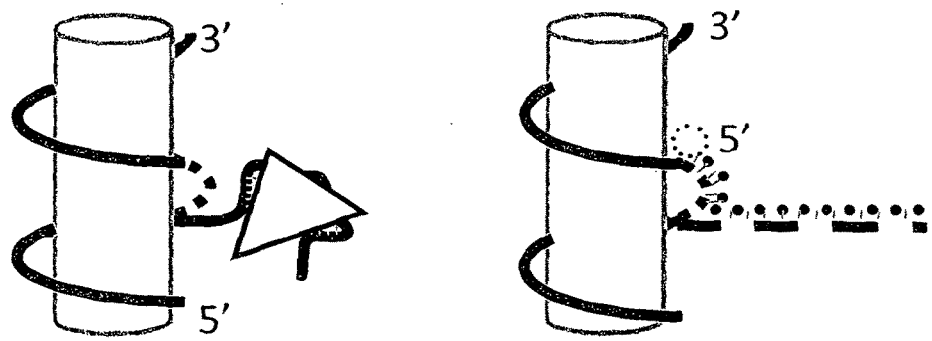
 = Target

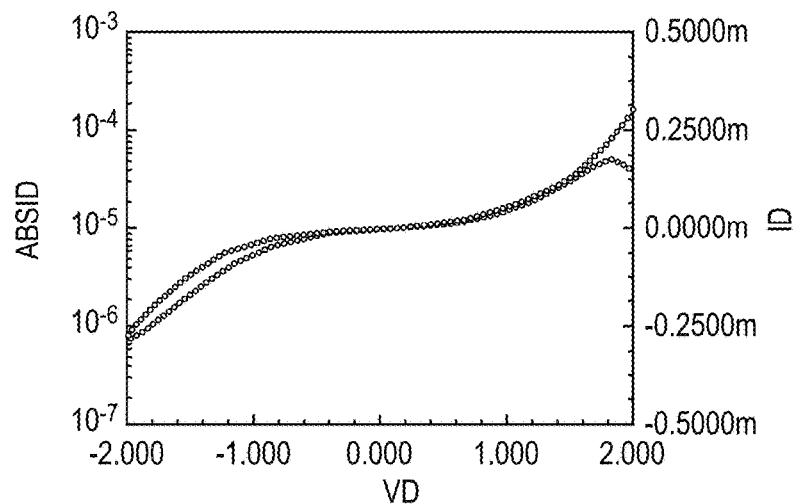
Figure 12
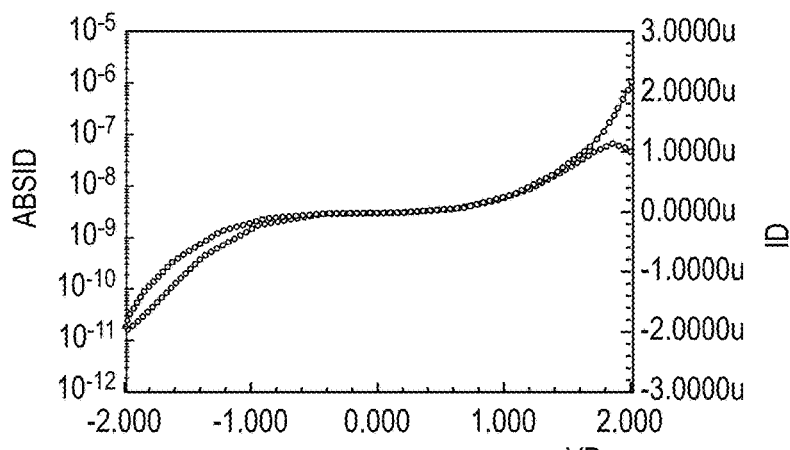
Figure 13
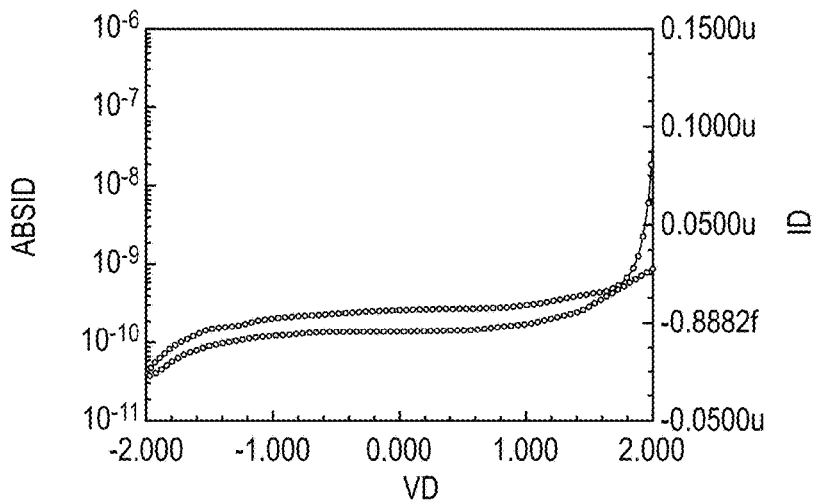

APTAMER COATED MEASUREMENT AND REFERENCE ELECTRODES AND METHODS USING SAME FOR BIOMARKER DETECTION

This invention relates to the detection of chemical, organic and biological analytes. More specifically, the invention relates to biomarker detection and is concerned with a device for reliably detecting the presence of low concentrations of molecular biomarkers in samples of fluid.

A promising field of application for such detection is in identifying diseases by way of Biomarker molecules. Existing approaches to the diagnosis of chronic diseases (for example tuberculosis) often rely on intricate laboratory tests on samples of blood, urine or tissue taken from a patient. In the exemplary case of tuberculosis (TB), the use of a 'sputum smear' test is common, relying on the identification of *Mycobacterium tuberculosis* bacilli using a microscope, or alternatively a tuberculin skin test.

It will be appreciated that it is not usually possible to carry out such intricate tests in close proximity to the patient, and therefore a network of laboratories is required, equipped with expensive testing equipment and highly trained staff. A complex logistics network is required to transport samples from the patient testing centres to the place of testing, and to deliver the results back to the patients after a delay.

It is known that chronic diseases such as tuberculosis are prevalent in developing countries, where the conditions described previously for successful testing are difficult to provide. Testing equipment might be too expensive for there to be an effective network of laboratories for the size of population or there could be a lack of skilled personnel to work in the laboratories. The transport of samples between the laboratories and the point of care could be difficult, and even upon delivery of a test result back to the point of care, it could prove difficult to find infected patients after intervals of up to several weeks, particularly in a transient population.

Insufficient access to the most advanced tests mean that tuberculosis detection programmes in disease-endemic countries are reliant on antiquated and inaccurate methods such as smear microscopy, solid culture, chest radiography, and skin testing. In the case of the legacy tuberculosis tests mentioned above, it is known that the tuberculin skin test has the disadvantage of being unable to distinguish between the latent and active stages of tuberculosis. The sputum smear test is only accurate in one half to three quarter of cases, requiring a large number of organisms in the sample and a skilled microscope operator able to distinguish between *M. tuberculosis* and other mycobacteria.

Molecular biomarkers offer an attractive new method of disease detection, compared with known techniques involving centralised laboratory testing. The rapidly advancing field of proteomics demonstrates that many diseases can be differentiated by testing for the presence of molecular biomarkers in bodily fluids such as blood plasma, urine or saliva.

One biomarker relevant to the detection of tuberculosis is neopterin, a catabolic product synthesised by macrophages (white blood cells) upon stimulation by the signalling molecule gamma-interferon. The presence of neopterin is known to indicate an inflammatory immune response, and one disease that causes production of neopterin is tuberculosis. Other macrophage activation markers are known, such as procalcitonin, C-reactive protein, soluble intercellular adhesion molecule 1, soluble urokinase plasminogen activator receptor, and Monocyte CDIIc66.

Another biomarker relevant to the detection of tuberculosis is thrombin, a coagulation factor which acts on fibrinogen to produce fibrin, a fibrous protein involved in the clotting of blood which also appears at heightened levels in patients suffering from tuberculosis. It will be appreciated that there exists a large and growing range of molecular biomarkers useful for disease diagnosis, and that the two biomarkers mentioned previously are examples. Other examples are Lysozyme and Nicotinamide adenine dinucleotide (NAD).

It will also be appreciated that the expression of different biomarkers can vary in dependence on the stage of the disease. For example, neopterin levels are increased at diagnosis based on the extent of the disease, and they decrease during and after treatment. A subsequent increase in neopterin levels is associated with relapse. Consistent quantitative longitudinal measurements are therefore of great diagnostic use.

Other biomarkers can be identified in microbial markers in sputum, microbial markers in urine, tuberculosis-specific T-cell function, and other macrophage activation markers. Indications of reactivation risk, and the eradication of a latent infection of tuberculosis, can also be predicted using for example gamma-interferon, or neopterin. Biomarkers can be used to judge vaccine efficacy, for example by monitoring polyfunctional T-cells.

Increased test specificity and predictive value can be achieved by combining an ensemble of non-specific biomarkers related to tuberculosis by measuring multiple parameters resulting from proteomics (the large-scale study of proteins), metabolomics (the study of chemical fingerprints that specific cellular processes leave behind), and transcriptomics (the study of mRNA used in gene transcription).

One way of identifying biomarkers is by the use of DNA-like molecules, as is shown for instance in WO 2007/001401 (Dupont/Boussard et al.), where oligonucleotides on carbon nanotubes are used. Aptamers are synthetic oligonucleotides (a short nucleic-acid polymer), ligands or peptides that can be isolated or created using for example the SELEX process against targets as diverse as small organic modules, toxins, bacterial and viral proteins, virus-infected cells, cancer cells and pathogenic organisms. They have defined shapes, and bind functional sites on their respective targets with affinities and specificities that often exceed those of the much more widely developed antibody reagents. Nucleic acid aptamers are easily isolated by a semi-automated totally in vitro process, removing the need for animal experiments. Further characterisation allows them to be minimised so that they can be made on the gram scale by synthetic chemical routes. They are easily concatenated with other nucleic acid sequences allowing bifunctional species to be created. Chemical functionalization of the aptamers to allow straightforward immobilisation and detection is also trivial. It is possible to synthesize an aptamer functionalized to conjugate to one of the disease-indicating biomarkers discussed above, such as thrombin or neopterin.

In order to expose aptamers to a solution possibly containing target molecules, they need to be bound to or "mounted on" a suitable substrate. To detect a binding event, it is advantageous if the substrate is conductive or semiconductive, and if it has a large specific surface area. One promising substrate is carbon nanotubes.

Carbon nanotubes are well known allotropes of carbon with a cylindrical structure. The aptamer may be attached to the nanotubes using either covalent or non-covalent approaches. For example, it is possible to attach a chemical "foot" structure to the non-biomarker-specific end of the aptamer molecule using a compound such as anthracene, which will then make contact with the surface of a carbon nanotube, coating it with a layer of biomarker-specific aptamer. In particular when the carbon nanotubes have semiconducting properties, when a carbon nanotube is coated with an aptamer and then exposed to the analyte that the coated aptamer binds to, the large number of binding events and the change in conductivity of the aptamer-coated carbon nano-wire or nanotube will be detectable by electronic means, for example by detecting a change in conductivity, capacitance, impedance, or inductance, potentially under high-frequency alternating current. Such aptamer binding events can also affect the conductivity of metallic nanotubes.

Such aptamer-coated carbon nanotubes as described in the previous paragraph can be applied across the gate of a Field Effect Transistor, in effect forming the channel. A carbon-nanotube FET (CNT-FET) with source, drain and back-gate contact, with the channel domain made of aptamer-coated carbon nanotube strands, is discussed in U.S. Pat. No. 7,854,826 (So et al./Korea Research Institute of Chemical Technology).

Although such detectors are promising, they are prone to variation in their accuracy and sensitivity. This is due to individual variation, variation in electrolyte concentration, temperature swings, geometry and other factors.

It will be appreciated that the chemical characteristics of the bodily fluids containing biomarkers of interest will vary; between different individuals, differing concentrations of electrolytes and other molecules such as proteins and enzymes in bodily fluids will be found. Without a method of controlling for these spurious effects, distinguishing for the presence of biomarkers is likely to be unreliable.

It is desirable to increase the reliability of sensors of this type, and in particular to provide a biomarker detector which can be used in the difficult context previously described to provide rapid and reliable disease detection in an inexpensive manner, and in a way that does not require the presence of skilled laboratory personnel.

SUMMARY OF THE INVENTION

According to the invention there is provided a device as claimed in claim 1 and a method as claimed in claim 26.

The invention uses a referencing system to reduce the likelihood of false biomarker detection events. Embodiments of the invention use an aptamer-coated conducting or semiconducting base or support, such as an array or deposit of carbon nanotubes, or a sheet-like structure such as graphene, or semiconducting DNA or other "nanowires" to form a sensor structure, and a second sensor structure that is essentially identical but is "capped", that is, the aptamer is prevented from recognising the target molecules, e.g. by being pre-coated with or conjugated or bound to the target molecules, or by being conjugated with a complementary DNA strands, or by being a mutant version differing in a few bases. Examples of conjugation may, amongst others, include the use of standard photo-cross-linking of the aptamer sequence to its target, or retention of a protective complementary oligo on the aptamer strand; one may also use an aptamer sequence variant that prevents binding. In the presence of target molecules or diagnostic biomarkers that bind to the aptamer, electrons are transferred and a change in conductivity of the support occurs. The semiconducting base could be said to act as the channel of a Field-Effect Transistor or CNT-FET. This change can be detected by suitable electronic circuitry, which may be built into the device, connected to the electrode system. The reading is then taken by comparing the "live" sensor with the pre-conjugated (reference) sensor. Since the two sensors of the pair are in identical molecular environments, i.e. inhabit the same measurement space, other variations e.g. resulting from electrolytes in the fluid samples are cancelled out.

Aptamers are a preferred option as a reasonably specific and cheap form of target-molecule detector, but other biomarker-receptive molecules or structures are envisaged, even antibodies or peptide aptamers for instance, provided that a sufficient electrical signal results from the binding process.

Often one wishes to measure several biomarkers simultaneously, because such an ensemble of biomarkers can more accurately indicate the presence of a chronic condition such as tuberculosis; in some embodiments, therefore, the detector has several such pairs of sensors and can easily be used to detect multiple biomarkers simultaneously and reliably.

More specifically, each of the biomarker-receptive detectors will also be placed next to, for instance, a biomarker-saturated detector. Such reference detectors will be identical to the biomarker detectors, with the important difference the reference electrodes will use aptamers which will already have been bound onto their target, e.g. by photo-cross-linking, use of a non-binding sequence variant or by retention of a base paired complementary strand, so that they are 'capped' to ensure that they do not react during a diagnostic test. That is, the aptamer is pre-bound with the target molecule or biological species. Apart from this difference, the reference detector is analysed for a change in conductivity, capacitance, etc. in the same manner as for the active biomarker detector. The purpose of this is that the multiple biomarker detectors, for example five in number, each now have an internal reference of a positive analyte detection event, subject to the same spurious effects that affect the entire detector. In this way, a 'control' comparison is provided in order to allow spurious first-order effects due to the variability between individuals or sampling conditions to be removed and thereby to calibrate the detection of each biomarker.

Various methods for coating supports with aptamers exist. As an alternative to the case with a carbon nanotube (or graphene) coated with biomarker-specific aptamer, it is possible first to functionalise a DNA strand—used purely as a support—with aptamer, and then to wind the functionalised DNA strand around a carbon nanotube substrate (or the strand can be wound first and then functionalised). The biomarker-specific aptamer and the capped aptamer can be attached to the DNA groups using click chemistry. Another possibility is to attach the aptamer to the nanotubes via a streptavidin-biotin linkage, where one of these elements is functionalised onto the aptamer and the other element is attached to the nanotubes via a covalent or non-covalent bond. Alternatively, a metallised DNA nano-wire could be coated directly with aptamer and capped aptamer. Another alternative could use conducting polymer coated with the aptamer or capped aptamer.

As mentioned previously, the binding of target biomarkers to their specific aptamers will cause a small but detectable change in the electrical characteristics across the electrodes. If need be, this signal can be amplified by making the electrodes the source-drain terminals of a CNT-FET, for instance. After a sample has been applied to the multiple biomarker-specific detectors and their accompanying references, the CNT-FETs are interrogated to determine the change in their electrical characteristics. Such measurements could take the form of a simple conductivity test with a DC source, or more complicated determination of impedance at certain frequencies or over a range of frequencies. The same test would be applied to the multiple reference detectors, allowing the spurious background effects present at the "live" detector to be removed from the genuine biomarker concentration measurement.

In one kind of construction, gold source and drain contacts of a CNT-FET are arranged as an etched interdigitated pattern on a silicon substrate, with the aptamer-coated carbon nanotubes laid over the top to form a kind of channel or semiconducting bridge. When using carbon nanotubes which have a mixture of conducting natures, it is preferable that the spacing of the interdigitated pattern is greater than the length of an individual nanotube to prevent the electrodes being shorted by one metallic nanotube acting as an impurity.

An alternative detection arrangement uses a polymer substrate, with gold electrode pairs laid out in a gridiron pattern and the aptamer-coated carbon nanotubes laid over the interdigitated pattern. Many variations are possible, as is known; in each case, pairs of sensor structures are used, with appropriate circuitry, to give a referenced result.

To perform the measurement process and obtain the measurements discussed above automatically, circuitry to interface with the CNT-FET array, including for example switches, signal sources, amplifiers, analogue-to-digital converters and microprocessors, is provided.

To ensure that there is sufficient test biological fluid, e.g. sputum, urine, blood etc., present on the sensor head before a measurement, logic circuitry is provided to provide a built-in self-test capability. Upon initial activation, the change of conductivity of each detector's reference electrode is recorded and compared against a known range, to ensure that sufficient fluid has been applied to the detector, and that subsequent measurements will be valid. The circuit performs a dry conductivity measurement on all tracks to verify the system's integrity. After the application of for example saliva or other biological fluid to the detector, the change in conductivity is verified to ensure that it is above a predefined level. Amplifying circuitry will be used to ensure that the dynamic ranges of the electrical signals are appropriate, for each sensor element. For some fluids, pre-treatment in a suitable buffer would be followed by selective filtration, e.g. to remove cell contaminants.

In order to satisfy the stated need for an inexpensive, rapid, point-of-care diagnostic sensor which can be operated by minimally trained personnel, the entire arrangement of detection substrate and circuitry discussed previously can be mounted inside a moulded body resembling known digital camera memory cards, for example. The sensor array is contained within a shallow trough to allow samples of bodily fluid to make contact with the aptamer-coated CNT-FET array. A detachable sealing film covers the active area of the detector to prevent the ingress of contaminants. It is envisaged that one side or end of the body moulding will connect the detection circuitry to a mobile handheld device such as a smart-phone, using one of the many data connectors and protocols available. In another embodiment the sensor moulding is inserted into a solution as a "dip stick" to measure other bodily fluids such as urine. Because of the small size of the detector, the mechanical support afforded by the socket should hold the detection card in a stable manner.

It will be appreciated that results generated by the detector can be downloaded onto a smart-phone or other handheld device, for collection, display or analysis. Additionally, the data can be forwarded via any accessible commodity radio transmission equipment and TCP/IP stack contained within the smart-phone to a centralised server.

BRIEF SUMMARY OF THE DRAWINGS

For a better understanding of the invention, and to show how it may be carried into effect, reference will now be made, by way of example, to the accompanying drawings in which:

FIG. 1 is a side view of an embodiment having a moulded body containing the substrate, sensors and sealable film;

FIG. 2 is a plan view of the layout of an arrangement of reference and sensor electrodes;

FIG. 12 shows the electrical characteristics of a nanotube device made by the deposition of nanotube-$(GT)_{10}$ complex.

FIG. 13 shows the device current (right axis, dark line) and the absolute device current (left axis, light line) as a function of gate voltage for "protected" and "unprotected" devices where the aptamer is against lysozyme;

FIG. 16a shows results from the as-made reference electrode (nanotubes functionalised by protected $(GT)_{10}$ thrombin aptamer), while

DETAILED DESCRIPTION

Figure 3:
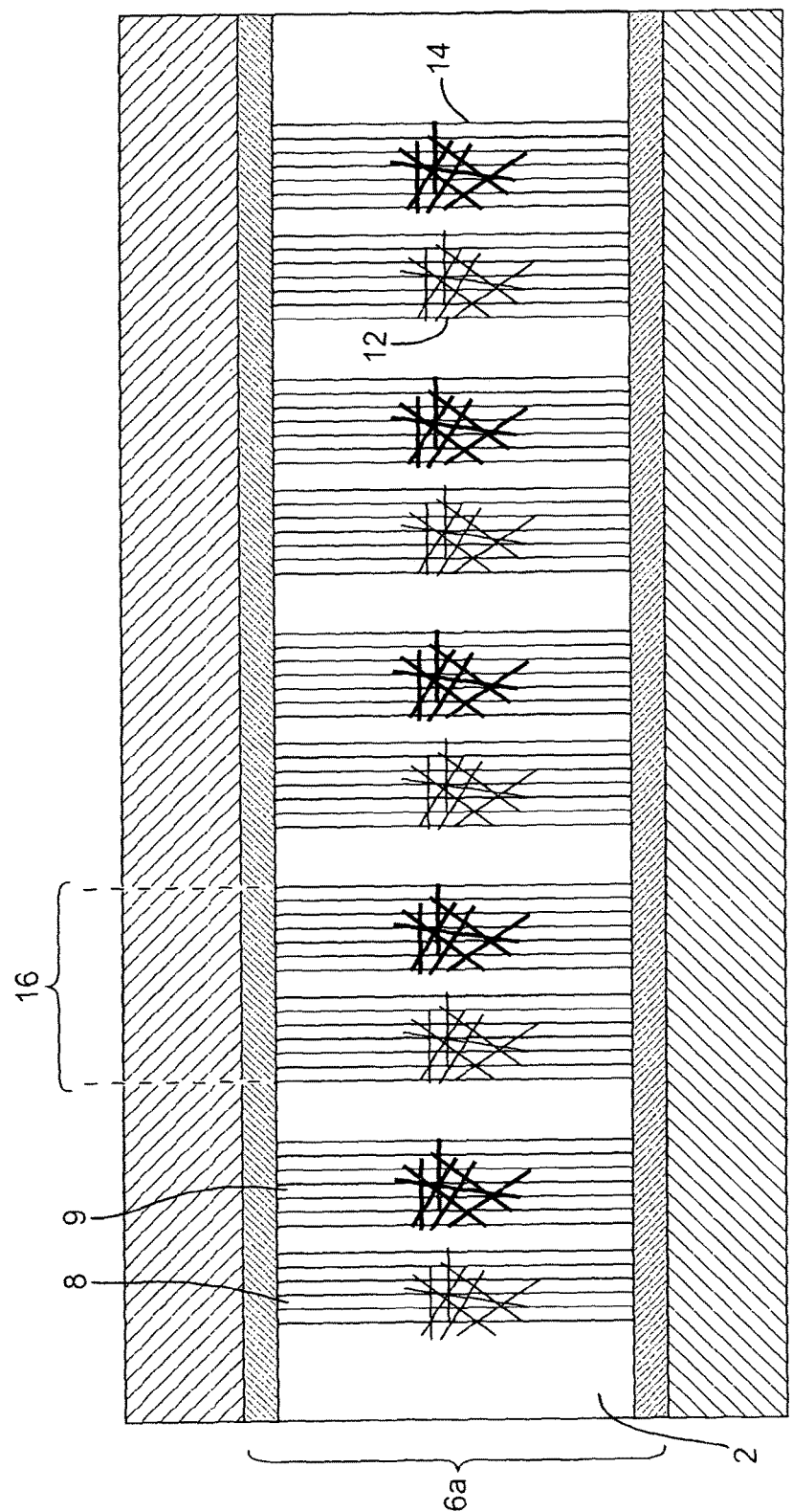
FIG. 3 is a plan view of an embodiment with five reference-sensor electrode pairs lying on a substrate.

A biomarker detection device 50 embodying the invention is mounted inside a body moulding 1 as illustrated schematically in FIG. 1. A substrate 2 is attached to the inside of the body moulding 1, and a plurality of planar contacts or electrodes 3, 4 is applied to the top side of the substrate to form sensors 8, 9. A shallow trough 6 can be formed to surround the contact areas of the substrate, to direct fluids to the contact areas at the start of a test, and to enable fluids to be retained at the contact areas during the detection process, in circumstances where the amount of fluid is small. A removable polymer sealing strip 7 is attached to the top surface of the body moulding with a weak adhesive, to provide a barrier seal against air and moisture in order to prevent the contact areas of the substrate from becoming prematurely exposed to contaminants or being degraded by oxidation or hydrolysis.

The arrangement of the electrodes on the substrate 2 is shown in more detail in the plan view of FIG. 2. The substrate 2 may consist of silicon, with preferably 300 nm thickness of silicon dioxide coating. For each sensor 8, 9, the electrodes 3, 4 are formed by alternately depositing and etching to leave parallel interdigitated contacts formed from a 20 nm thick chromium adhesion layer underneath a 100 nm thick gold layer. Typically, the linear tracks are spaced 10-50 µm apart and are connected alternately to electrode contacts 30, 31. These contacts could be labelled "source" and "drain", though, strictly, in most embodiments, the device is not really a FET. The interdigitated electrodes are alternated in perhaps twenty or thirty pairs (the drawing is schematic and shows only a few pairs), giving a total width of perhaps 300 µm, and a comparable height (in the drawing). Terminals 10, 11 collect current from the interdigitated electrodes 3, 4 respectively. The electrode pairs of each sensor may be placed in close proximity to each other, say 500-1000 µm.

A conducting or semiconducting sensor structure 12 capable of conjugating with a target biomarker of interest is coated onto the first of the pair of interdigitated contacts 3, 4, forming what will be referred to as the "measurement" sensor. The further sensor structure 14 of substantially identical nature, but already conjugated with the biomarker targeted by the measurement sensor is applied to the second of the pair of interdigitated contacts 9, forming what will be referred to as the reference sensor. When interfaced with appropriate electronic circuitry to be described subsequently, the pair of measurement and reference sensors together forms a detection pair 16 for one biomarker of interest.

The sensor structure 12 capable of conjugating with the target biomarker comprises carbon nanotubes functionalized with a specific aptamer created by coating the substrate 2 and therefore the interdigitated contacts 3, 4 with a layer of carbon nanotubes. The aptamer can be a short (say about 40 nucleotides) length of DNA or RNA, or a peptide fragment, for instance. In the case where the substrate 2 is silicon, a thin insulating layer is applied to the electrodes and a back-gated carbon-nanotube "FET" is formed having terminals which one may label source and drain, a channel formed by the carbon nanotubes, and a gate formed by a doped layer in the silicon. If amplification by back-gating is not necessary, the gate need not be present.

In embodiments where a network of semiconducting nanotubes is used as the sensor structure, the spacing of the electrodes should be designed to ensure that, even if a sample of semiconducting nanotubes contains conducting nanotube impurities, statistically there is unlikely to be a path of conducting nanotubes bridging the electrode, shorting the sensor. The CNTs may be of the order of 1-10 µm long if the tracks are 10-50 µm apart. Their structure and function is described later in more detail.

The spaces defined by the interdigitated electrodes in effect form a very wide channel between two electrodes. The collected signals from the electrodes of each interdigitated pair are fed to suitable circuitry (not shown). Here the signal from the capped sensor 9 is compared with the exposed or "measurement" sensor 8. Whereas the absolute level of the signal can be expected to drift or vary with conditions, the difference (or ratio, or other comparison) gives a reliable reading. Since the two sensors are close together, they are affected equally by their environment.

For certain applications, it is often necessary to detect at the same time an ensemble of biomarkers, often referred to as a biosignature or "fingerprint", for instance of a disease, to improve the likelihood of a correct detection event. FIG. 3 illustrates a plan view of a biomarker detector similar to that in FIG. 2 but having a linear arrangement of five detection pairs each with its measurement 8 and reference 9 sensor on a common substrate 2, with their interdigitated electrodes shown very schematically; it will be appreciated that a larger or smaller number of detection pairs could be deployed according to the precise ensemble of biomarkers of interest, which will vary with the intended application of the device. The linear array of detection pairs here coincides with an extended shallow trough 6a, to ensure that fluid samples can be correctly contained over the array of detection pairs.

In general, biomarkers are indicative of, but not 100% specific to, say, a disease. However, by obtaining quantitative readings of a suitable set of biomarkers a good degree of confidence can be achieved. For instance, TB may be identified using four biomarkers: Neopterin, which indicates Inflammatory processes and oxidative stress in cells; Procalcitonin, which distinguishes bacterial diseases as compared with viral diseases; Lipoarabinomannan (LAM), which tends to distinguish latent vs. active TB, and C-Reactive Protein (CRP), which again tends to be associated with inflammatory processes and oxidative stress. See Tuberculosis 4, Biomarkers and diagnostics for tuberculosis: progress, needs, and translation into practice; Robert S Wallis, Madhukar Pai, Dick Menzies, T Mark Doherty, Gerhard Walzl, Mark D Perkins, Alimuddin Zumlat. Published Online May 19, 2010; DOI:10.1016/S0140-6736 (10) 60359-5: http://www.mossmanassociates.com/TB %20Biomarker %20report %20Lancet_2010.pdf A device such as that shown in FIG. 3 can present a result in a single reading.

As an alternative to this multiple individual measurement-and-reference system, multiple reference systems can be templated in a regular pattern for a single measure and reference result.

Alternative track layouts can be used for the detection area when it is fabricated on a plastic substrate, with the contact area formed from a number of parallel track pairs arranged in a grid pattern. In such an embodiment, the contacts may be formed from deposited gold, silver or carbon applied by an inkjet printing process. The interdigitated tracks can be straight or winding or convoluted.

To manufacture the back-gated or top-gated FET forming the semiconductor sensor structure 12, the channel domain between the source and drain contacts (spaced approximately 10 µm apart) must be coated with a functionalized channel material, preferably CNTs, in particular SW (single-walled) CNTs, and preferably predominantly semiconducting, though these are more expensive. One simple way of achieving this end is to coat the electrodes with a solvent suspension of SWCNTs.

In one exemplary technique the SWCNTs are modified with β-Cyclodextrin (β-CD) which does not require prolonged heating, filtration, and washing of the CNTs, which can cause damage. The SWCNTs are dispersed in a β-CD solution with sonication, typically resulting in a 2 mg/ml, suspension. An aliquot of the suspension is then applied to the contact area in the trough 6 of the substrate 2. To ensure that the alignment of the functionalised SWCNTs 12, 14 across the interdigitated contacts 3, 4 is as uniform as possible, it is possible to apply an electric field across the contact area of the substrate 2 as the aliquot evaporates, but the main requirement is that the nanotubes are uniformly distributed.

Another exemplary technique for accurately depositing carbon nanotubes between electrodes based on dielectrophoresis is given in Suhiro et al. ("Fabrication of a carbon-nanotube-based gas sensor using dielectrophoresis and its application for ammonia detection by impedance spectroscopy", J. Phys D: Appl. Phys. 36 (2003) L109-L114). In this method, multi-walled CNTs suspended in ethanol are sonicated. An interdigitated chromium electrode array fabricated upon a glass substrate is surrounded by a silicone-rubber spacer to form a sealed chamber. The carbon nanotube suspension is continuously circulated over the electrodes, which are simultaneously excited by a 100 kHz, 10 V pk-pk AC voltage, resulting in the multi-walled carbon nanotubes bridging the gaps between the electrode fingers. It will be appreciated that other methods of depositing carbon nanotubes between electrodes could be employed.

Following the application of the functionalised carbon nanotubes 12, 14 to the contact area, they are subjected to a 'pegylation' treatment. Pegylation is known to those skilled in the art as the process by which polyethylene glycol (PEG) chains are attached to proteins, thereby increasing the molecular mass of the proteins. However, in this application, the polyethylene glycol is deposited directly onto the surface of the carbon nanotubes, covering the areas of the nanotube that have not been functionalised with an aptamer or a DNA strand. The intention of this treatment is to ensure that proteins not specific to the functionalised aptamer cannot bind to any unfunctionalised part of the sensor, thus introducing additional spurious effects into the measurement. This has the effect of improving the sensitivity of a functionalised nanotube when exposed to a fluid sample containing a diversity of protein species. The substrate 1 and/or the trough 6 may also be treated to pegylate their surfaces to prevent absorption of species which may interfere with the measurement process. A typical PEG treatment leaves a layer between 2 and 3 nm thick on the surface of the sensor. The process can be performed either on the substrate surface after nanotube deposition, or in solution before the nanotubes are coated onto the contacts.

It will be appreciated that the details of the fabrication of the measurement 19 and reference 20 electrodes of a detection pair 16 are identical, with the exception of the SWCNT coating applied to the contacts. Therefore the fabrication of the measurement and reference electrodes could take place simultaneously until the later stage of SWCNT coating. At this point, two separate solutions of SWCNTs are applied, the first solution to the electrodes of the measurement sensor 19, with the reference sensor masked, and the second solution to the reference sensor 20, with the measurement sensor masked. The solutions differ in that the carbon nanotubes suspended in the first solution applied to the measurement electrode 19 are functionalised aptamers capable of binding to a target biomarker. The carbon nanotubes contained in the second solution applied to the reference electrode are functionalised with an aptamer that is already saturated (pre-bound, conjugated or capped) with the target biomarker.

In operation, a device is prepared with a capped sensor structure 14 on one area of substrate with electrodes 4 and an uncapped or bare sensor structure 12 on the other substrate area, with electrodes 3. The device is exposed to a solution to be measured, by immersion or application of a drop of the analyte, such as a fluid. Electrolyte and other content may cause a change of conductivity of the sensor structures 12, 14 but this is the same for both. Only binding events cause a differential change. The resulting signal is analysed by suitable circuitry of the device. A test can be run for a set time, such as 30 seconds, taking a reading automatically at the end, so as to give a measure of concentration in the electrolyte.

One could also detect the target analyte (causative molecule) in air or non-biological systems if the analyte is VX or similar.

A typical detection event will consist of measuring the doping such as hole or electron transfer that occurs in the binding event between the immobilized aptamer on the surface of the carbon nanotube, and the target biomarker. A large number of such doping events (e.g. electron transfers) caused by binding events will modulate the source-drain current flow in the "CNT-FET", an effect that can be further influenced by the applied gate-voltage.

The device can also act as a time-averaging sensor in the manner of a radiation monitor; that is, it remains in place and keeps conjugating to available targets, and only displays a signal if the time average conjugation, which may be related to concentration, is above a certain value, or it integrates over time to measure an exposure greater than a threshold.

As mentioned in relation to FIG. 3 and previously in the description, a device with an array of sensor pairs will detect an ensemble of biomarkers, with each biomarker corresponding to a detection pair. For example, a detector able to detect five biomarkers will consist of a substrate 2 with a row 26 of five detection pairs. For a device targeting five biomarkers, ten separate SWCNT coatings would be applied, the first set of five coatings representing the 'live' coated SWCNTs applied to the measurement electrodes, and the second set of coatings related to the capped-aptamer coated SWCNTs applied to the reference electrode.

As mentioned above, in order to detect specific molecules the carbon-nanotube bases first need to be "functionalized". One way of doing this is for single-walled carbon nanotubes (SWCNT) to be directly functionalized by non-covalent attachment of biomarker-specific aptamers to the nanotubes' outer wall.

Figure 4:
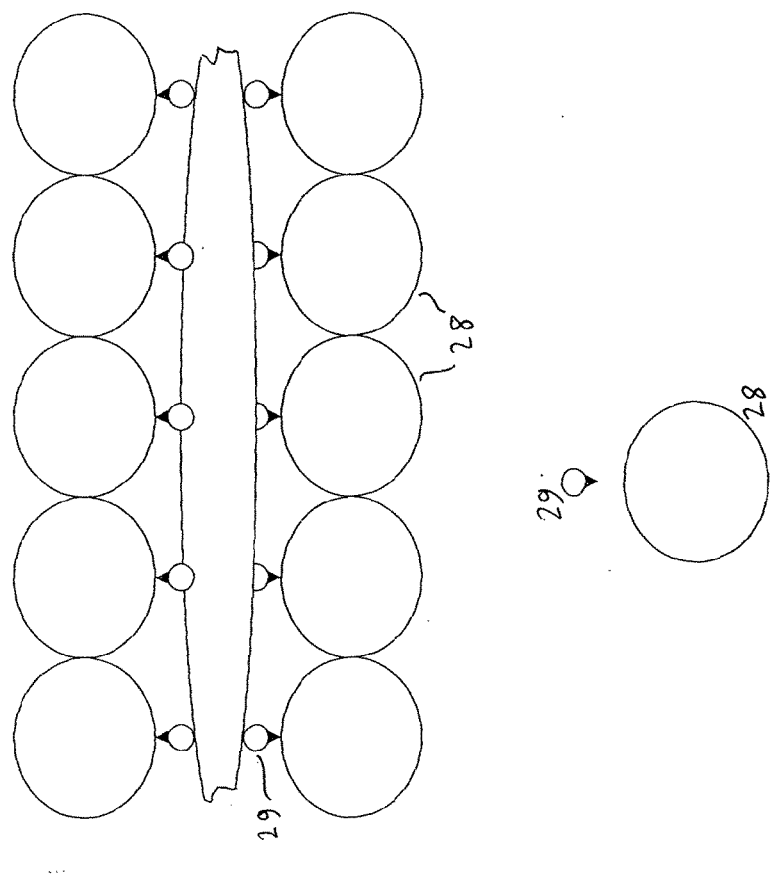
FIG. 4 provides end-on and plan schematic views of the way in which an exemplary aptamer is attached to a carbon-nanotube backbone.
Figure 4:
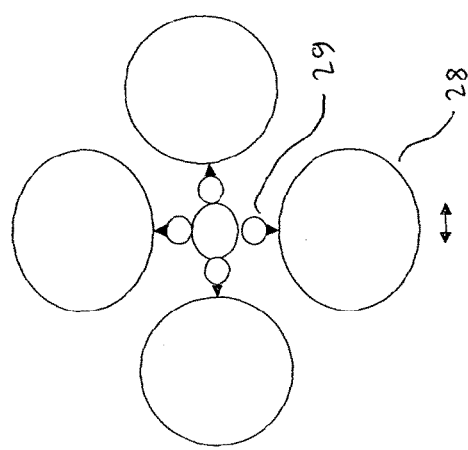

Preferably, aptamers are immobilised on the surface of the carbon nanotube using a substance with a high affinity for the carbon nanotube, for example anthracene or a single stranded DNA support strand (which acts as a "foot"). The carbon nanotube is then said to be functionalized to the biomarker targeted by the aptamer. The highly schematic FIG. 4 provides axial and plan views of a carbon nanotube 27 with a generic functionalized aptamer 28 immobilised on the external wall of a carbon nanotube using anthracene 29. However, it will be appreciated that many methods are known in the art for nanotube functionalisation, for example carboxylation followed by esterification, or click chemistry as described below. It should be noted that the drawing is schematic, and in reality a CNT would be much longer than is implied, while aptamers in particular are unlikely to be spherical.

A typical carbon nanotube might be 1000 nm long with a diameter of 1.25 nm, and that the respective effective diameters of the aptamer and the anthracene are 3 nm and 0.1 nm. Under these assumptions, four functionalized aptamers can be attached to a circumference of a SWCNT, and 330 along the length, leading to an estimate of a total of 1320 functionalized aptamers per SWCNT.

Figure 5:
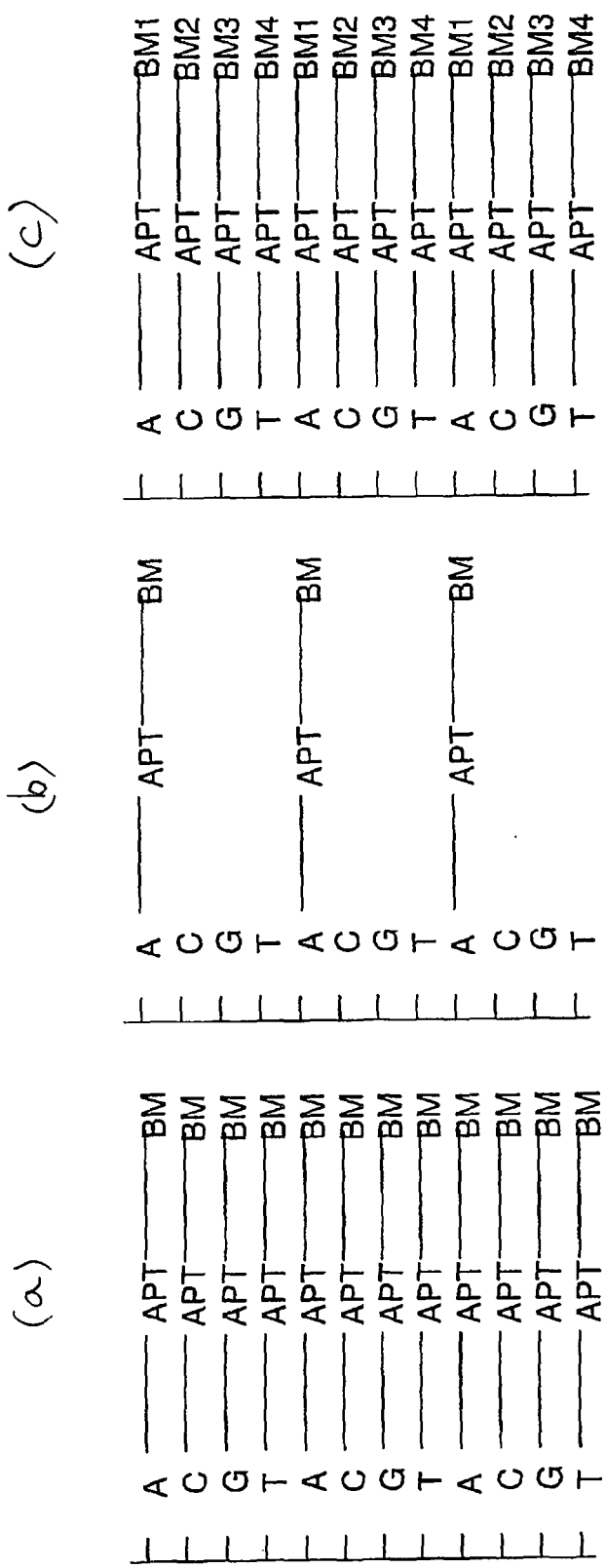
FIG. 5 shows three different embodiments of aptamer-biomarker arrangement on a DNA backbone.

In a second type of method of functionalizing carbon nanotubes, a single-stranded DNA is modified by 'click' chemistry to support aptamers, as shown in FIG. 5. This strand is then wound around a single-walled carbon nanotube.

'Click chemistry' describes reactions between functional groups which result in a stable linkage, exhibit minimal thermal cross-reactivity with other functional groups, react to completion, are free of appreciable amounts of side products, and proceed under benign reaction conditions.

The click chemistry paradigm can be applied to modification of nucleic acids, and it is known that it can be used to label oligonucleotides with fluorescent dyes, sugars or peptides; to cyclise DNA; and to join oligonucleotides to DNA.

In a preferred embodiment the attachment consists of an polynucleotide foot, preferably alternating GT sequences of $(GT)_n$, where the number of GT repeats, n, is 5 to 50, most preferably n=10. The GT sequence includes a pendant alkyne functional group onto which an azide-modified aptamer may be attached through 'click' chemistry. Most preferably, the aptamer is attached to the middle of the foot structure forming a T-junction to ensure good contact with the nanotube.

Alternatively, the carbon nanotube may be functionalised directly with the aptamer using 'click' chemistry, in the absence of the intermediary DNA wound around the carbon nanotube.

Preferably, in both the cases where the aptamer is attached to the polynucleotide foot or directly onto the CNT, the aptamer is protected during the chemical conjugation by a complementary molecule, such as a DNA strand. Once the conjugation is complete, the protecting molecule is removed. Such an approach reduces the undesired functionalisation of the recognition part of the aptamer during chemistry and reduces the probability of undesired adsorption of the aptamer onto the nanotubes. The protecting sequence is sufficiently complementary to the aptamer to ensure sufficient binding during the functionalisation so that the aptamer is protected but may contain mismatched sections in order to reduce the melting point of the complex to allow facile removal. Urea or pH changes may also be used during the removal process to reduce the temperature required.

In order to saturate the surfaces of the nanotubes to prevent unspecific binding of the target aptamers excess $(GT)_n$ may be introduced.

FIG. 5 shows a DNA strand wound around a SWCNT or MWCNT, or other conducting medium. Three alternative arrangements of aptamers attached to a DNA backbone with 'click' chemistry are illustrated. In (a), a biomarker-specific aptamer is conjugated to each of the Adenine, Cytosine, Guanine or Thymine bases of a DNA strand. In (b) an aptamer is conjugated only to the Adenine base, for example, leading to a lower density of aptamers compared to the backbone in (a). In (c) up to four aptamers targeting different biomarkers have been conjugated with the DNA. It will be appreciated that the aptamers conjugated with the backbone may be of the active variety (not conjugated with their target biomarkers), or may already be conjugated with their target biomarkers (capped). In this way, strands of DNA suitable for winding around carbon nanotubes forming either the measurement or reference sensors can be prepared.

A hybrid of the functionalized DNA and carbon nanotubes is formed by winding the functionalized DNA strands around the nanotubes. It will be appreciated that either in the embodiment concerning direct attachment of aptamers to a carbon nanotube, for example via carboxylation, or in the embodiment describing the winding of a DNA strand around a carbon nanotube, the aptamers attached either directly to the nanotube or to the DNA strand are in the measurement sensor unconjugated and in the reference sensor conjugated with their target biomarker or otherwise capped (they are 'uncapped' or 'capped' respectively).

Figure 6:
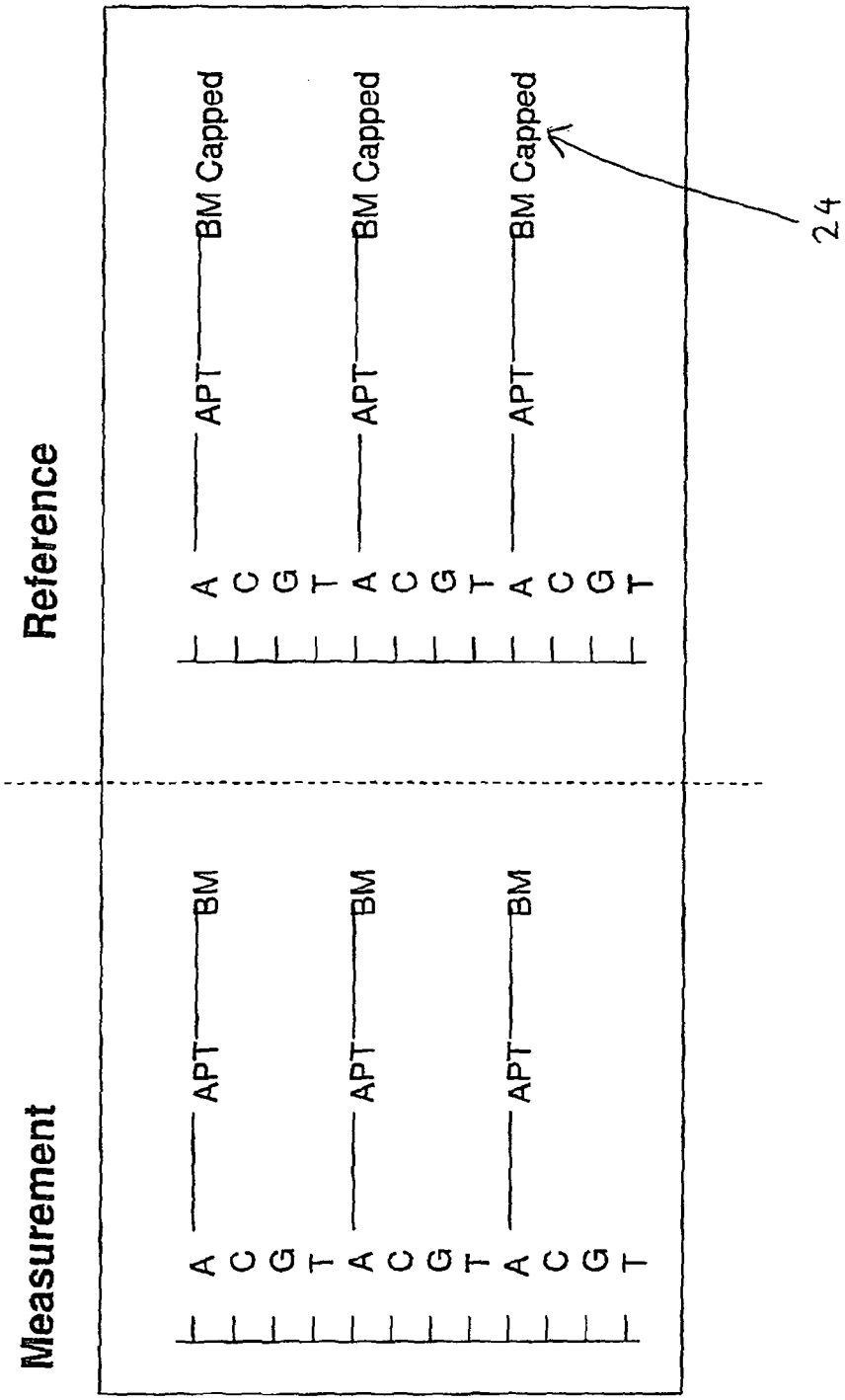
FIG. 6 shows the different arrangement of capped and uncapped biomarker as applied to the DNA backbone of the reference and sensor electrodes.

FIG. 6 is a diagram corresponding to FIG. 5(*b*) and showing a pair of sensor structures, measurement and reference, with the reference structure pre-bound with biomarker and the measurement structure having some biomarker bound to it during the measurement process.

The diagrams show aptamers bound to the bases, but in fact it is likely to be the hydrophobic bases that bind to the CNT with the backbone facing outwards, so that the aptamers would be bound to the backbone.

Figure 7A:
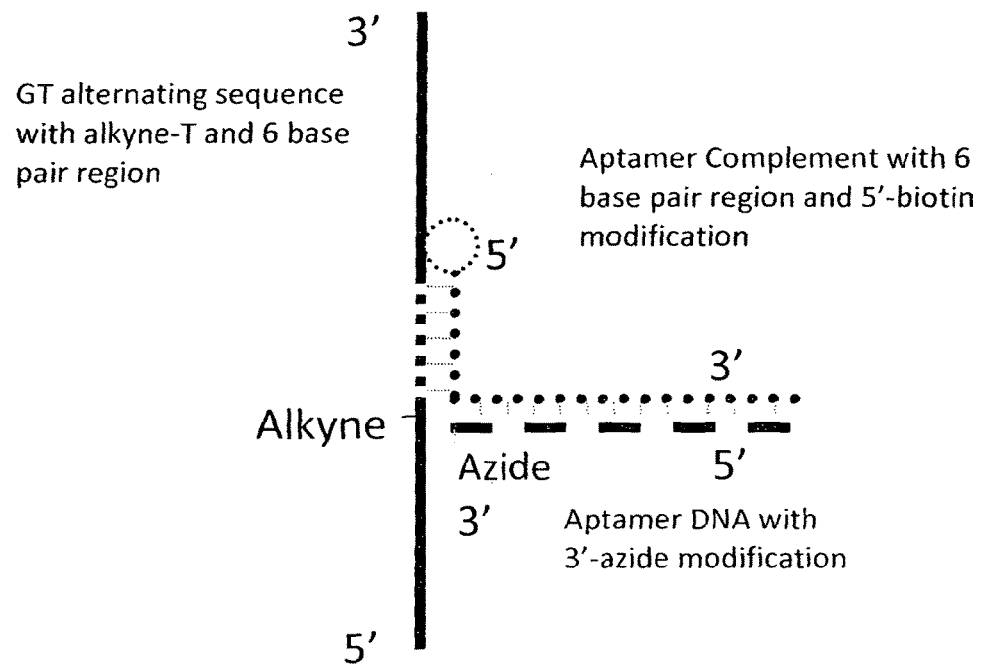
FIG. 7 shows a sequence of steps using click chemistry to form the functionalised CNTs.
Figure 7B:
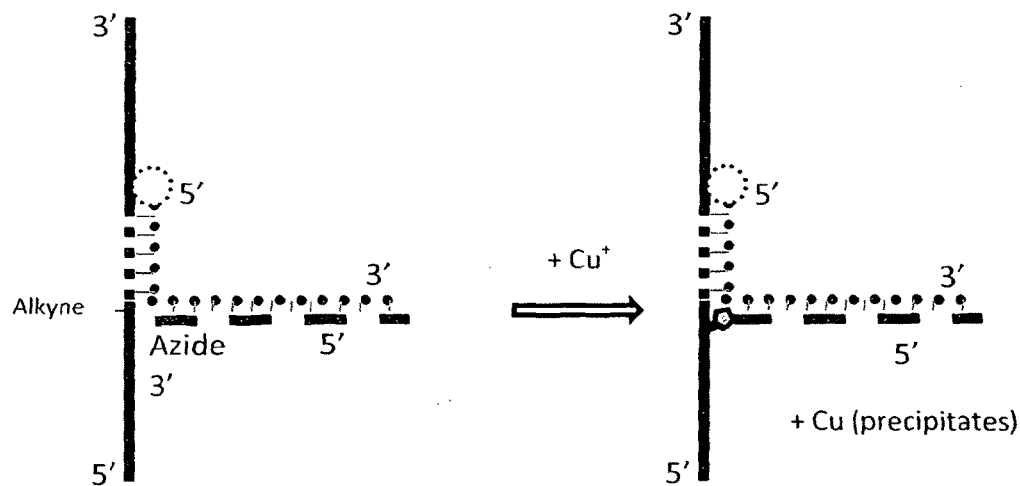

FIG. 7 shows a way of preparing the aptamer-DNA contains for the CNTs. A DNA strand (vertical) composed mostly of an alternating GT sequence, including a single alkyne-T adjacent to a short unique sequence, is provided on the one hand, and on the other the desired aptamer DNA (horizontal) with 3'-azide modification, protected by a fully complementary DNA strand with the added base pairing region to align on the supporting DNA strand (foot) and a 5'-biotin modification. Click conjugation (second panel of FIG. 7) takes place at the alkyne-azide location on addition of $Cu^+$. The DNA is then dispersed with CNTs and suitably treated, e.g. by agitation, causing the CNTs to disperse evenly. Then the suspension is incubated with streptavidin coated onto magnetic beads and heated briefly. The streptavidin binds to the biotin (panel 3) and the beads can then be removed (panel 4), pulling the protective complement from the aptamers and making the active CNTs ready for use.

Meanwhile the other part of the batch, for the reference sensors, keeps the aptamer protection. The solutions are then dispersed over the interdigitated electrodes. It is preferable to carry out the latter step after the aptamer binding, so that all possible sites are accessible for binding. As shown in the final diagram, the effect of the target binding (left) can then be compared to the reference or inactive sensor (right) in identical chemical conditions.

In another embodiment, the sensor may be formed using the techniques commonly associated with the area of printed electronics. In this case, a substrate may be formed from a plastic polymer, for example polyethylene terephthalate (PET), polyethylene naphthalate (PEN), poly-4-vinylphenol (PVP), or PEG. Tracks, of metal or carbon, are deposited on the plastic substrate, and the carbon nanotubes are deposited between them using the method described subsequently.

Referring again to FIG. 2, it will be understood that means for measuring electrical characteristics between the interdigitated source 30 and drain 31 contacts of the reference and measurement electrodes should be provided. As described above, the measurement sensor 8 has main electrode terminals 30 and 31 and a gate, somewhat analogously to a FET, but the coating of aptamer-coated carbon nanotubes is applied between the "source" and "drain" terminals to prepare the gate area of the FET. The terminals of the device can be connected to electronic stimulation 37 and measurement 38 means to measure the electrical characteristics between the source and drain electrodes.

For example, the stimulation means 37 could assume the form of a voltage source, and the measurement means 38 could assume the form of an ammeter, allowing an assessment of the conductivity variation between the source and drain electrodes 30, 31.

It will be appreciated that other electronic circuitry such as instrumentation amplifiers and variable current or voltage sources could be used during the measurement process. It will also be appreciated that the stimulation 37 and measurement 38 means could be fabricated onto the same substrate 2 that forms the substrate for the contact area, if it is silicon, or alternatively could reside on a separate board in close proximity to the silicon substrate, with the source 30 and drain 31 contacts being connected by bond wire.

By changing the stimulation and measurement means, the variation of other parameters could be measured across the source 30 and drain electrodes 31. For example, the stimulation means could assume the form of a high-frequency source which could either stimulate the contacts of the SWCNT with a single frequency, or sweep across a wide frequency range. This would allow an assessment of the impedance across the source 30 and drain 31 electrodes. Similarly, means could be provided for measuring the resistance, capacitance or inductance.

When considering the provision of detection circuitry, it will be realised that circuitry identical to that used for the measurement electrodes 34 can also be provided to measure the characteristics of the reference electrode simultaneously.

Figure 8:
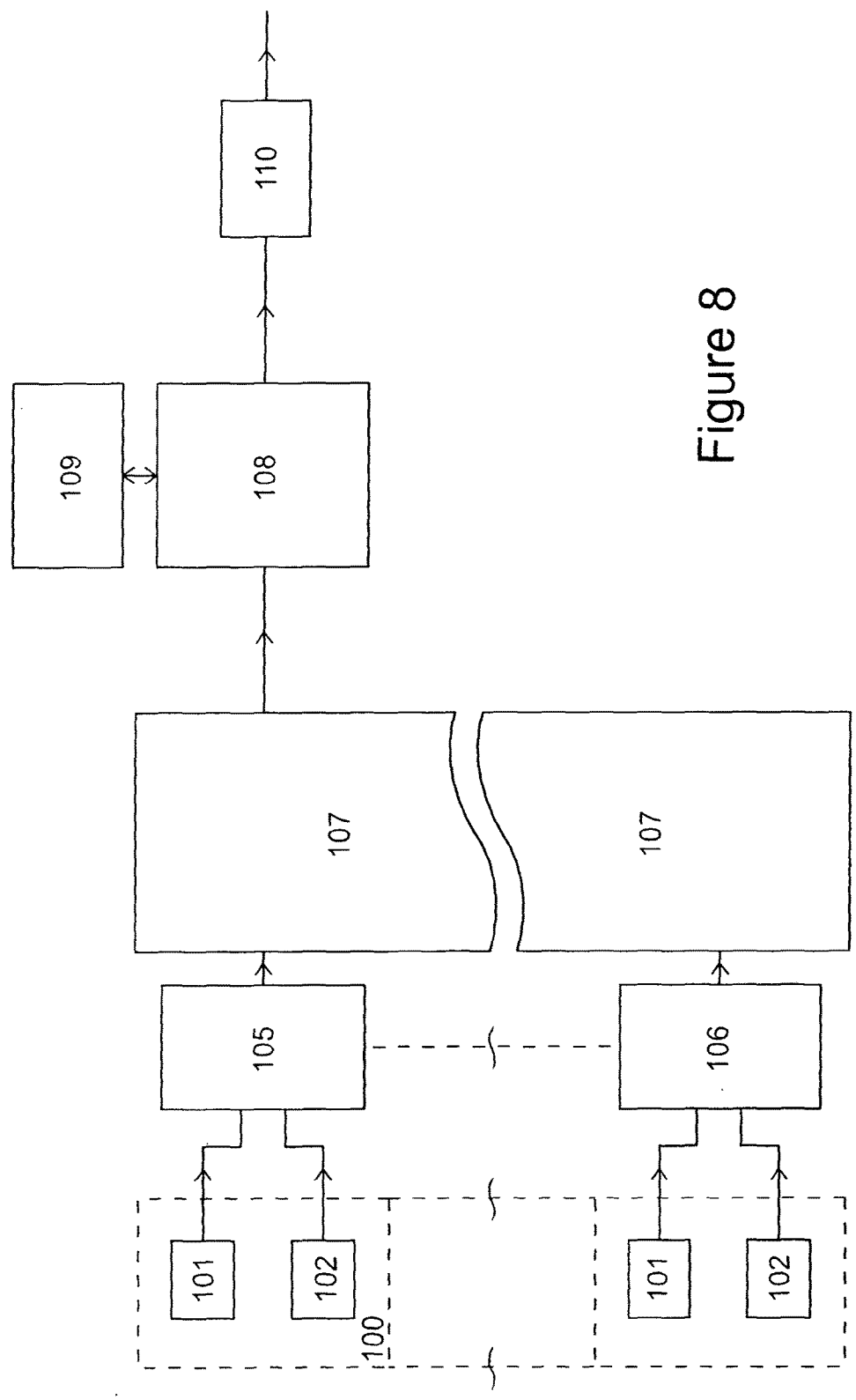
FIG. 8 shows a control system connected to the sensors, for further processing the results and transmitting information to and from the processing means.

As shown in FIG. 8, the signals representing variation in conductivity, impedance, resistance, capacitance, or inductance, for example from a detection pair 100 comprising a measurement electrodes 101 and reference electrodes 102 can be transmitted to calibration means 105. In the case where the signals are analogue, the decision-making means could be an analogue subtraction. However, it would be possible to digitise the signals from the measurement and reference sensors using an analogue-to-digital converter and perform the subtraction between them digitally. The corrected signal 111 is then output. As mentioned previously, a plurality of detection pairs is provided to enable the detection of an ensemble of biomarkers. It will therefore be appreciated that a commensurate number of calibration means will need to be provided.

A subsequent decision-making means 107 is provided into which the calibrated signals are input. The decision-making means assesses the ensemble of calibrated signals from the plurality of detection pairs, and detects for a condition. If the condition is satisfied, the decision making means indicates this by outputting a logical signal. It will be appreciated that other information relevant to the detection process could be output, for example raw measurements of conductivity for each nanotube.

It will be appreciated that the circuitry described above may be fabricated on a printed circuit board (PCB), and connected to the sensor substrate using bond-wire or some other means. In the preferred embodiment, the sensor substrate is single-use disposable and easily plugged into, and removed from, a multi-use measurement unit which contains the measurement circuitry and output devices. This embodiment enables the sensor substrates to be kept in optimum storage conditions, e.g. sterile environment and temperature control. Alternatively, it will be appreciated that a proportion of the circuitry could be fabricated directly onto the sensor substrate, with the remainder occupying a PCB connected to the substrate. Additionally, the PCB could be connected mechanically and electrically to a connector, which for example could include a USE connector, or a micro USB connector, although it will be appreciated that many other types of data connector could be used, including wireless connectors.

Experiments were carried out to test the feasibility of the system, and measurements made, as will now be described.

Step 1: Production of the DNA-Aptamer i) DNA Synthesis

DNA was synthesised using step-wise solid phase synthesis on an ABI 394 DNA/RNA Synthesiser using DMTr chemistry protection for 5'-OH and a β-cyanoethyl-protected 3'phosphite.

Azide functionality was introduced using 3'amino CPG which was then converted to 3'azide using azidobutyrate NHS ester chemistry. An alkyne-functionalised "T" phosphoramidite was used to incorporate the alkyne group within the DNA sequence ii) Purification of Oligonucleotides after Cleavage and Deprotection Using HPLC.

Oligonucleotides were purified using either:
RPLC using a gradient of 100% 50 mM Ammonium Acetate pH 6.8 to 100% 50 mM Ammonium Acetate in 50% acetonitrile, at 55° C.
Ion exchange chromatography using water to 100% 1.2M NaCl at 60° C.

iii) Conversion of 3'-Amino Group to 3'-Azide:
Azidobutyrate NHS ester was dissolved in MaCN. 3'-amino-DNA dissolved in 0.1M carbonate/bicarbonate pH 9. Azidobutyrate NHS ester was added to dissolved oligonucleotide and reacted at room temperature for 2 hrs. To concentrate 2 volumes of cold ethanol was added, incubated at −80 C for 20 minutes and pelleted (4,000 g, 30 mins). Redissolved DNA was desalted into 18.2 mΩ water and lyophilised.

iv) Click Chemistry
(refer to FIG. 7.)
The alkyne-labelled DNA (in water) was added to the azide labelled DNA to dissolve. CuBr solution containing 0.1 M TBTA in DMSO/t-butanol 3:1 (v/v) was incubated at 45° C. for 2 hours[1, 2]. Reaction was diluted with water, desalted into 18.2 mΩ water and lyophilised.

v) Verification of DNA Synthesis and Click Products
Synthesised DNAs were subjected to negative mode electrospray ionisation mass spectrometry to verify correct masses.
Click reaction products were labelled at the 5' phosphate using γ-[32P]-ATP [3]. These were analysed on 10% denaturing SDS polyacrylamide gel to show successful "click" conjugation.

REFERENCES

1. Kocalka, P., A. H. El-Sagheer, and T. Brown, Rapid and efficient DNA strand cross-linking by click chemistry. Chembiochem., 2008. 9(8): p. 1280-5;
2. El-Sagheer, A. H. and T. Brown, Click chemistry with DNA. Chem. Soc. Rev., 2010. 39: p. 1388-1405;
3. Sambrook, J., Molecular Cloning; A Laboratory Manual. 2nd ed 1989, Cold Spring Harbour: Cold Spring Harbour Laboratory Press.

Protocols and Reagents
www.glenresearch.com
www.linktechnologies.co.uk

Step 2: Oligomer Protection, removal.
The scaffold or protecting strands were synthesised with a 5' biotin group enabling their removal post-CNT immobilisation of the T-piece via the ssDNA GT "foot"

fragment by brief (2 min) incubation above the respective Tm in the presence of streptavidin-coated magnetic beads. After exposure to a magnet the supernatant containing the free aptamer strands attached to the CNTs via the "feet" were used for coating the electrode elements.

Step 3: Construction of the Reference Electrode.

Examples of reference electrodes were created by retention of the aptamer hydrogen-bonded complementary or scaffold strands, thus blocking formation of the active conformation of the aptamer stand.

Alternatively, the aptamer strands were synthesised with a photoactive cross-linking group and covalently linked to its target in the presence of excess target by UV illumination.

Figure 9:
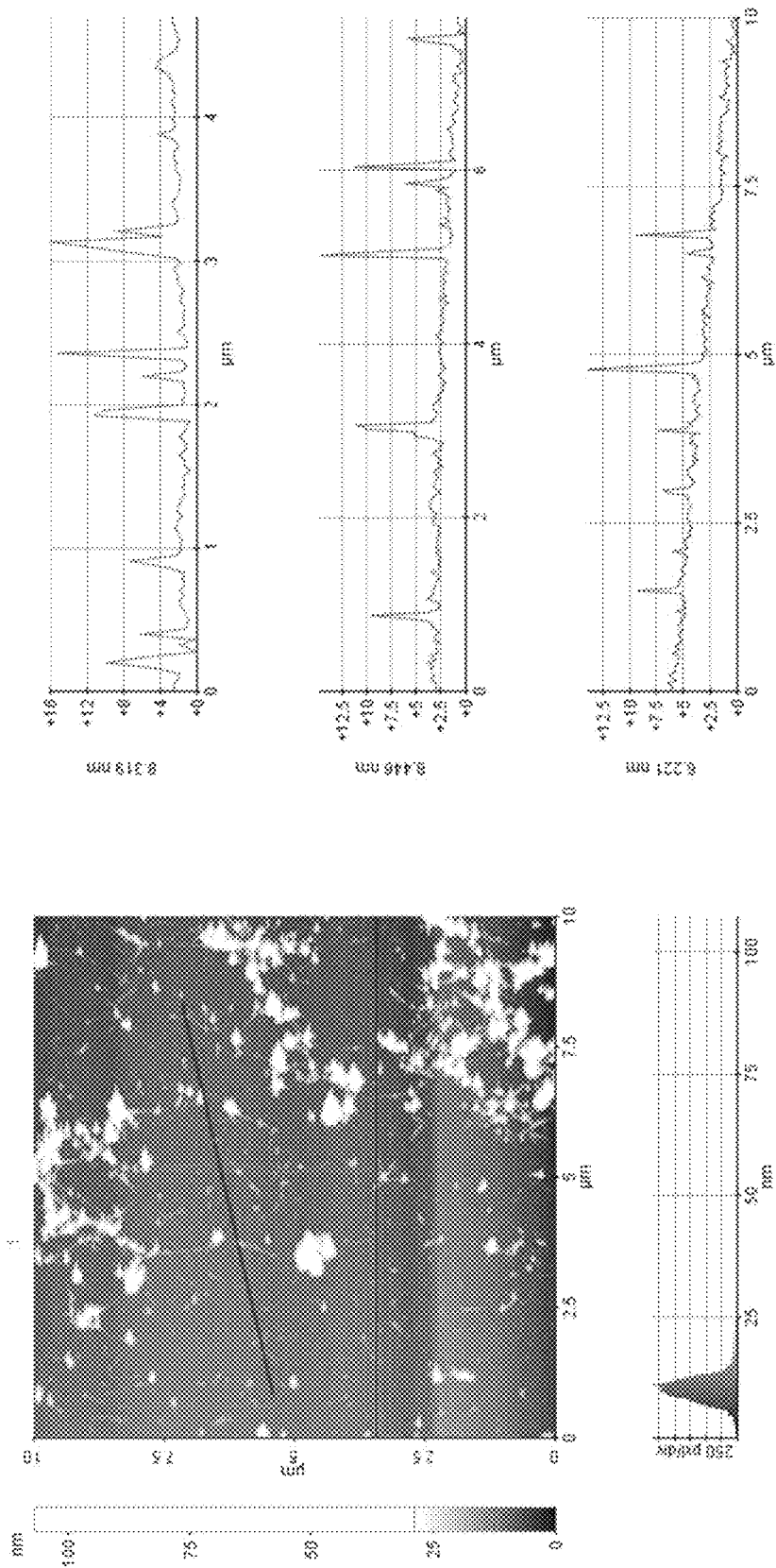
FIG. 9 shows atomic force microscopy of single-walled carbon nanotubes which have been dispersed using single-strand herring sperm and then dried on a substrate.

An initial exaperint fwas performed in order to demonstrate the uniform dispersion of DNA-coated nanotubes, using frozen herring sperm DNA solution FIG. 9 is an atomic force micrograph of such a nanotube dispersion dried on a silica substrate showing the dispersed DNA-coated nanotubes and the formation of a percolated network. The images and line scans confirm that that the nanotubes are well-dispersed and can dry to form the conductive networks required for the sensor.

Step 4: Dispersion of Nanotubes in $(GT)_{10}$ in Phosphate Buffer Solution (PBS).

For making the aptamer-presenting nanotubes, a synthetic DNA, namely $(GT)_{10}$, conjugated to a capped aptermr strand, was used. Frozen $(GT)_{10}$ solution at a concentration of 3.25 mg/ml was defrosted at room temperature. 115 microliters of the DNA solution was sonicated for 15 min.

0.19 mg of as-received nanotube powder (Nanointegresis, semiconducting) was added to 1 ml of PBS and sonicated for 80 min in total using ultrasonic probe using 40 min at 15 W with additional 0.5 ml of PBS. The nanotube dispersion was diluted to 0.19 mg in 1.5 ml of PBS and sonicated in an ultrasonic bath for 2 h prior to mixing with DNA.

The DNA solution (115 microliters) added to the CNTs dispersion and sonicated in ultrasonic bath. PBS was then added to the dispersion (285 μl) until the dispersion reached the required nanotube concentration. Overall, a ratio 2:1 (DNA:SWNT w/w) was achieved with cDNA:0.2 mg/ml and cCNTs:0.1 mg/ml. The dispersions were sonicated vigorously in ice water causing the sample to turn dark red. The dispersions were sonicated for a total of 2 h, with ice being added to the sonic bath every 20-30 min to prevent the temperature rising above 8° C. Finally, the dispersions were gently centrifuged at 3300 rpm for 1 h and then filtered using a 1-micron syringe filter.

Step 5: Deposition of the Nanotube Dispersion onto the Electrodes.

Figure 10A:
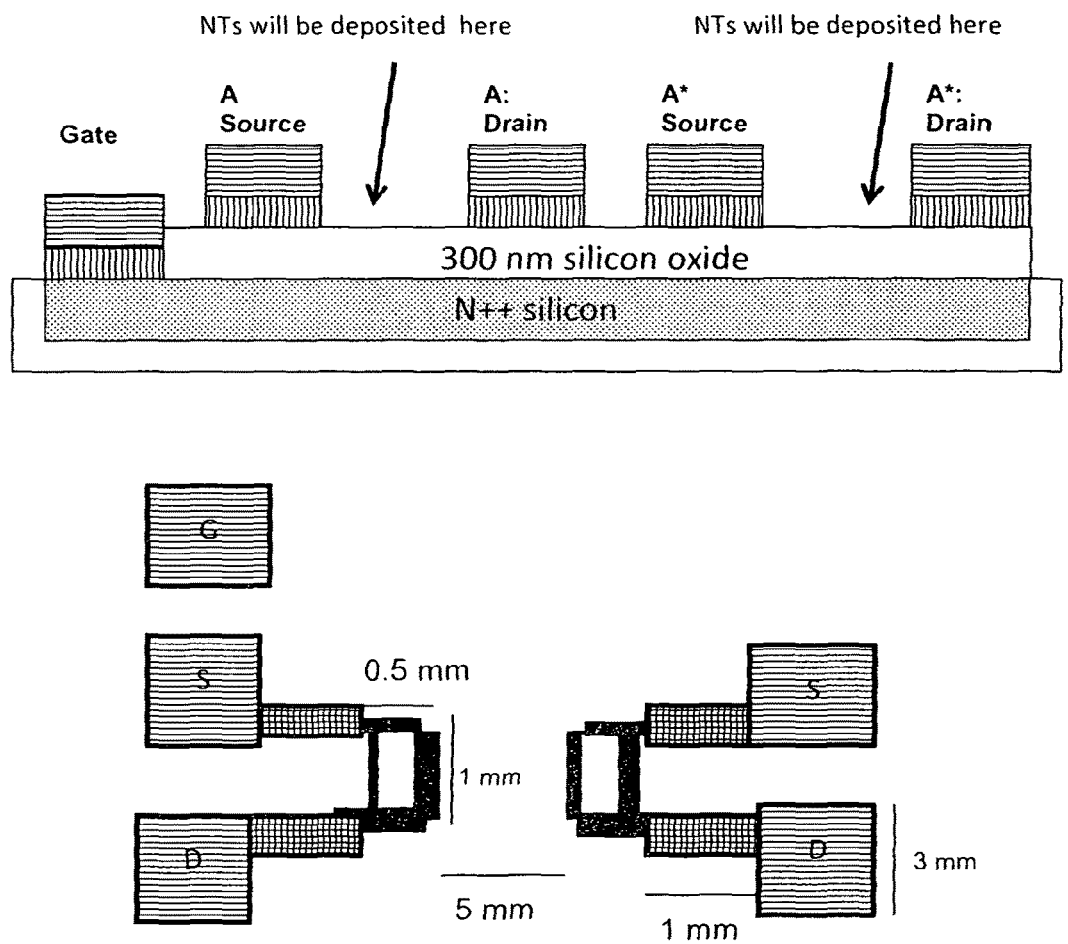
FIG. 10a shows a schematic of the inter-digitated electrodes used to measure the electrical properties of the nanotube networks, including those suitably functionalised to detect the target analyte.

Electrodes were produced using lithographic techniques. The electrodes comprised of inter-digitated electrodes as shown in FIG. 10a. In this drawing, the top diagram is a cross-section of the part of the inter-digitated electrode design, the middle is a plan layout of the reference and sensor pair. The top view is a cross-section of one of the electrodes, while the bottom diagram is a plan view of a pair of electrodes, one of which would be used a "reference" electrode and the other as the "measurement" electrode. The rectangular pads labelled G, S and D are used to connect the electrodes to the measurement circuitry. Note that the labelling denoted here is for a transistor setup with a source, drain and gate contacts. However the same electrode design maybe used in a non-transistor situation where the current between the two inter-digitated electrodes are measured, with or without a gate bias.

Figure 10B:
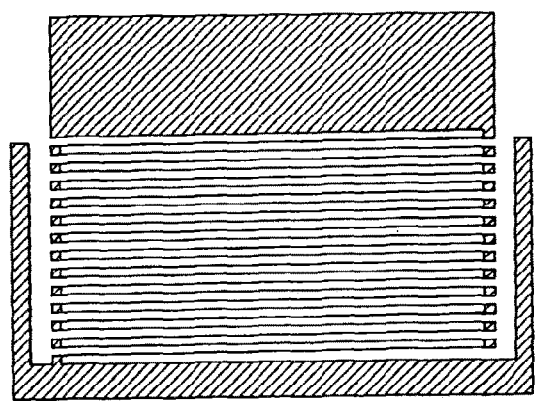
FIG. 10b shows a schematic of an optical micrograph of the sensor interdigitated electrodes.

FIG. 10b is a schematic of an optical micrograph of the sensor interdigitated electrodes. The gold tracks are 10 microns wide and spaced by 10 microns.

Bare electrodes were rinsed with methanol, acetone and IPA was blown with $N_2$ and cleaned in UV-$O_3$ for 30 min. The electrodes were isolated on substrates using hydrophobic pen. A 2 μm drop of CNTs-DNA dispersion was then deposited onto the electrodes.

Results 1: Electrical Measures of Nanotubes-DNA Complex on the Electrodes.

Semiconducting nanotubes (NanoIntegresis) were dispersed with single-strand DNA using the protocol discussed with reference to FIG. 9. Dispersions of 0.1 mg/ml, 0.05 mg/ml, 0.007 mg/ml and 0.001 mg/ml nanotubes were prepared and deposited on the electrodes. A voltage of 2 V was applied across the electrodes and the gate voltage varied as the electrode current was measured.

Figure 11:
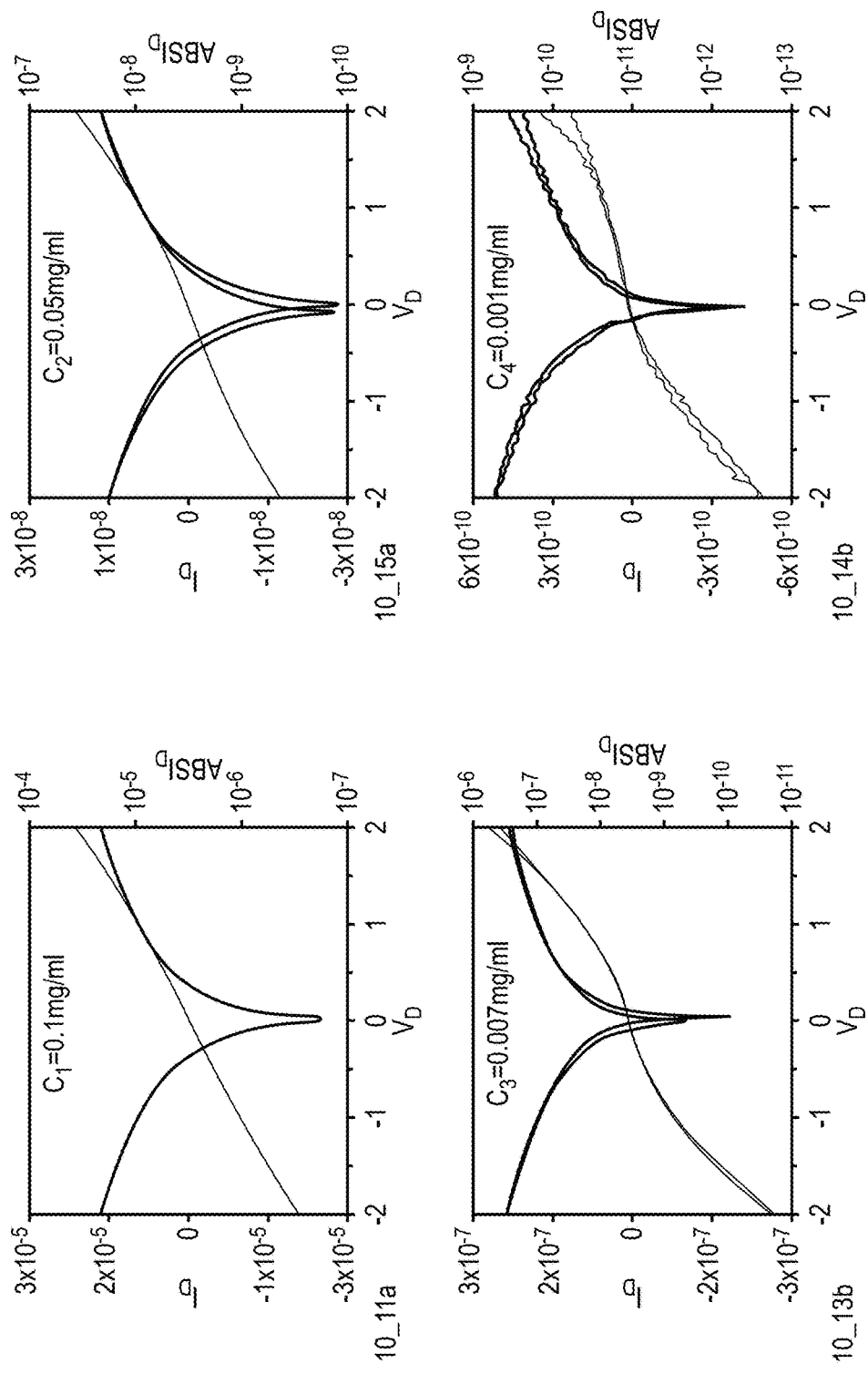
FIG. 11 shows the electrode current as function of gate voltage for nanotube networks formed by the deposition of herring-sperm DNA wrapped nanotubes.

The results are shown in FIG. 11, which has the device current (left axis) and the absolute device current (right axis) as a function of gate voltage for various initial dispersion concentrations. The absolute value of current is V-shaped because of the bipolar nature of the CNT network. The initial concentrations in terms of nanotubes are as denoted in the title of the graphs. It was found that a concentration of about 0.007 mg/ml of nanotubes gives a reliable coverage without excessive risk of short-circuits. Short-circuits arise from metallic nanotubes; it is difficult and expensive to ensure pure semiconducting nanotubes, so the sample used contained about 10% metallic forms. Shorting was also prevented by having sufficient difference in the separation of the electrodes compared to the length of nanotubes used-as as described earlier.

Results 2: Electrical Measures of Nanotubes-$(GT)_{10}$ Complex on the Electrodes.

Semiconducting nanotubes (NanoIntegresis) were dispersed with single-strand DNA using the protocol discussed in Step 4. Dispersions of 0.1 mg/ml nanotubes were prepared and deposited on the electrodes as discussed in Example 4. A voltage of 2 V was applied across the electrodes and the gate voltage varied as the electrode current was measured.

FIG. 12 shows the device current (right axis, dark line) and the absolute device current (left axis, light line) as a function of gate voltage.

Results 3: Electrical Measures of Nanotubes-$(GT)_{10}$ Complex on the Electrodes.

In this experiment, aptamers were applied to the DNA. Semiconducting nanotubes (NanoIntegresis) were dispersed with single-strand $(GT)_{10}$-lysozyme aptamer T-piece at using the protocol discussed in Example 2. These samples are designated "protected" and still have the conjugated protecting strand attached to the aptamer. A second set of samples, designated "unprotected", were produced by heating the single-strand $(GT)_{10}$-lysozyme aptamer T-piece dispersion at 70° C. for 15 minutes prior to introducing them to the nanotube dispersion. The dispersions were prepared at a concentration of 0.007 mg/ml and 2 microliters were deposited on the electrodes as described in Example 4.

FIG. 13 shows the device current (right axis, dark line) and the absolute device current (left axis, light line) as a function of gate voltage for: LEFT—the "protected" device where the aptamer is still conjugated to its protective strand, and RIGHT—the "unprotected" device where the aptamer has had the conjugated strand removed. The aptamer used in this case was against lysozyme.

Some examples will now be described of thrombin-specific sensors.

Example 1: CNTs/Deprotected $(GT)_{10}$ Thrombin Aptamer

Frozen protected $(GT)_{10}$ thrombin was defrosted at room temperature. 100 microliters of this solution was diluted in 900 microliters of PBS to give an approximate concentration of $(GT)_{10}$ thrombin of 1.2 mg/ml. The solution was incubated at 90° C. for 2 min and cooled down slowly at room temperature to ensure that all the oligomers were base paired before dispersion.

0.6 mg of nanotube powder from Nanointegris was placed into 2 ml of PBS and sonicated using ultrasonic probe for 80 min at 15 W. The CNTs dispersion was sonicated in ultrasonic bath for 30 min prior to mixing with DNA. 1 ml of the $(GT)_{10}$ thrombin solution was added to the nanotube dispersion and sonicated in ultrasonic bath. PBS was then added to the dispersion (3 ml) until the dispersion reached the required nanotube concentration. This process resulted in DNA:SWNT w/w of cDNA:0.2 mg/ml, cCNTs:0.1 mg/ml.

The dispersions were sonicated vigorously in ice water causing the sample to turn black. The vial was suspended centrally in the bath, at a depth of 20-40 mm, with ice around the edges of the bath preventing heating of the sample.

The dispersions were sonicated for a total of 2 hours, with ice being added to the sonic bath every 20-30 min to prevent the temperature rising above 5° C. Once the nanotubes had been functionalised by the $(GT)_{10}$ thrombin aptamer, the protecting group was removed by rapidly heating to 70° C. and harvesting the protecting group using magnetic streptavidin beads.

The dispersions were then gently centrifuged at 3300 rpm for 1 h and then filtered using a Whatman syringe filter. The dispersions were then diluted to the required concentration using PBS. In this example the dispersion was diluted to give a concentration of 0.007 mg/ml of nanotubes.

The electrodes were cleaned and isolated using a hydrophobic pen. A 2 microliter drop of dispersion was placed on the electrode and allowed to dry. The final devices consisted of a network of nanotubes covered in the deprotected thrombin aptamer. This electrode is the "measurement" electrode.

Figure 14:
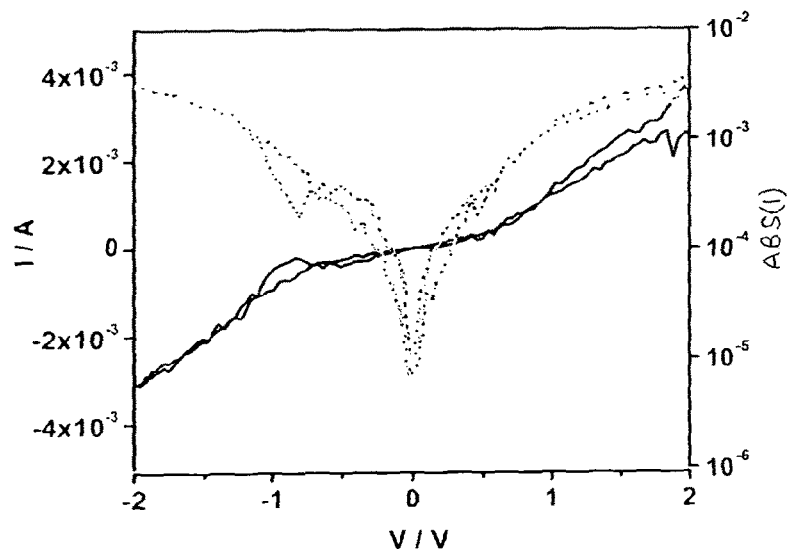
FIG. 14 shows the device characteristics an embodiment with deprotected $(GT)_{10}$ thrombin aptamer.

The current (ID) between the source and drain electrodes, or rather the main electrodes, was then measured as a function of gate voltage (VD) as shown in FIG. 14. The device shows a semiconducting behaviour. The device is a sensor made by CNTs functionalised by deprotected $(GT)_{10}$ thrombin aptamer. Measurements were made after drying. The current between the electrodes (I, left axis, dark line) as a function of gate voltage (V). (The right hand axis and light line denote the absolute current (ABS(I)).)

Example 2: CNTs/Protected $(GT)_{10}$ Thrombin Aptamer

The electrode was made as described in Example 1. However, the protecting group was left in place so that the final devices consisted of a network of nanotubes covered in the protected thrombin aptamer. This electrode is the "reference" electrode.

Figure 15:
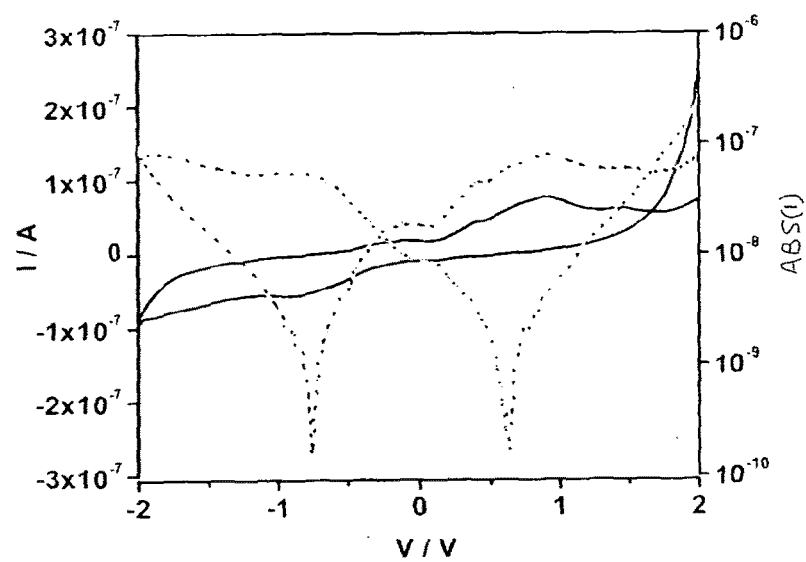
FIG. 15 shows a characteristic for a setup as in FIG. 14 but with the protecting group left in place.

FIG. 15 shows the current between the main electrodes (ID) as a function of gate voltage (VD). As with the deprotected electrode, a semiconducting behaviour was observed. In this device, an electrode made by CNTs is functionalised by protected $(GT)_{10}$ thrombin aptamer. Measurements were made after drying. Measurements were made after drying. The current between the electrodes (I, left axis, dark line) as a function of gate voltage (V). (The right hand axis and light line denote the absolute current (ABS(I)).)

Example 3: Comparison of the Response of the Reference and Measurement Electrodes Measurement electrodes were produced as described in Example 1 and reference electrodes were produced as described in Example 2. The electrical characteristics of the electrodes were measured (FIG. 16). 100 nM thrombin was then introduced to the electrodes, allowed to dry and the electrical properties were measured again (FIG. 17). No significant change was observed in the reference electrode after the introduction of the thrombin, whereas in the "measurement" electrode, the current increased by a factor of ~4 at 2 V drain voltage.

Figure 16A:
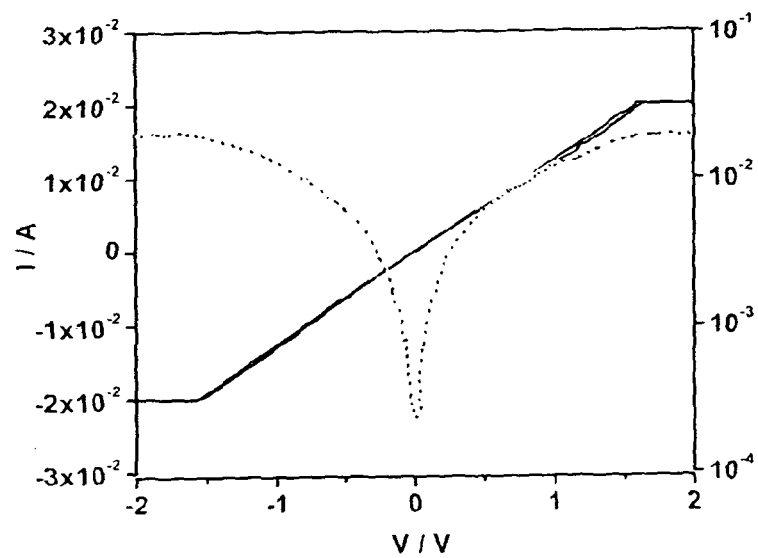
Figure 16B:
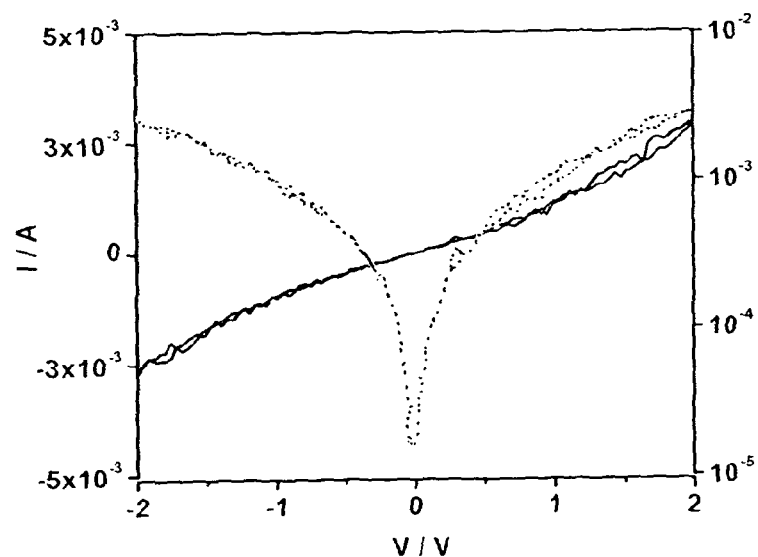
FIG. 16b shows the deprotected result.

FIG. 16a shows the as-made reference electrode (nanotubes functionalised by protected $(GT)_{10}$ thrombin aptamer) and FIG. 16b shows the as-made measurement electrode (nanotubes functionalised by deprotected $(GT)_{10}$ thrombin aptamer). Measurements were made after drying. The current between the electrodes (left hand axis, "I", dark line) is plotted as a function of gate voltage (V). (The right hand axis and light line denote the absolute current, ABS(I).)

Figure 17A:
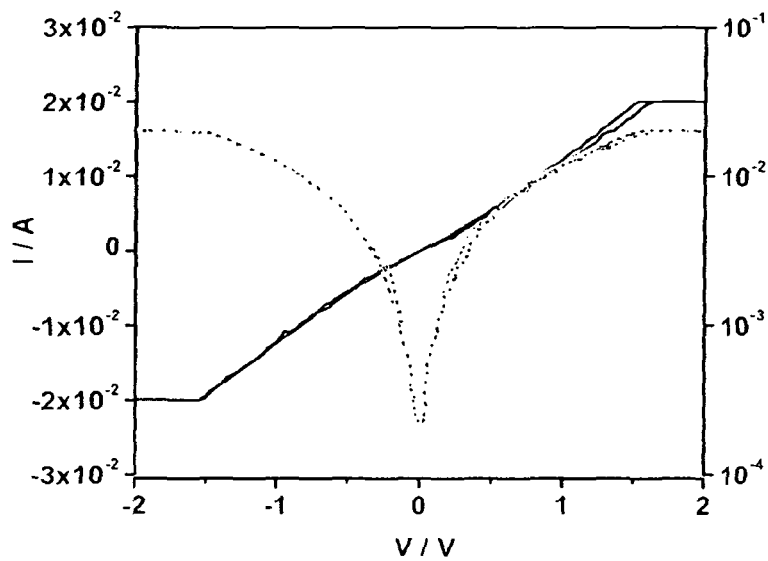
FIG. 17a shows results for the as-made reference electrode (nanotubes functionalised by protected $(GT)_{10}$ thrombin aptamer) and FIG. 17b shows the deprotected equivalent.
Figure 17B:
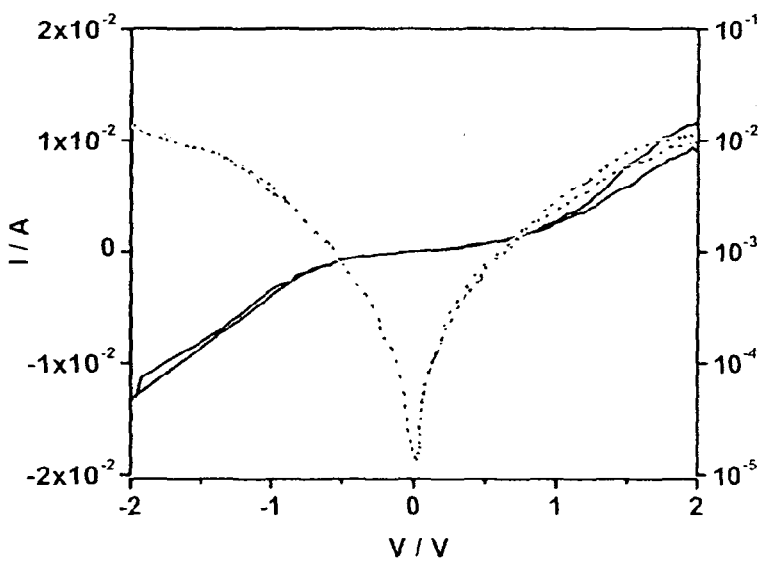

FIG. 17a shows the as-made reference electrode (nanotubes functionalised by protected $(GT)_{10}$ thrombin aptamer) and FIG. 17b shows the measurement electrode (nanotubes functionalised by deprotected $(GT)_{10}$ thrombin aptamer) after the deposition of the 100 nM thrombin and subsequent drying. The current between the source and drain of the electrode (ID—dark line) is plotted as a function of gate voltage (VD). (The right-hand axis and light line denote the absolute current.)

Although the invention is anticipated to be useful for detecting tuberculosis, it will be appreciated that it could be adapted to detect biomarkers indicative of many other conditions as well. Additionally the technique may be used to detect molecular species of non-biological origin, as exampled by, but not limited to, chemical-warfare agents, narcotics and explosives. Possible fields of interest are:

Human/veterinary medicine, in particular infectious diseases such as human/bovine TB;
Homeland security, including biohazards such as anthrax, tetanus, nerve gases, and explosives such as TNT, 2,4-DNT, 2-6-DNT etc;
Law Enforcement, in particular drugs including Cannabinoids, benzoylecgonine;
Health & safety—detection of noxious gases/vapours, naphtha, hydrocarbons;
Process & Quality Control;
Very high value products such as fragrances e.g. musk (galaxolide);
General Measurements, Instantaneous or continuous or cumulative:
  Gas, vapour, liquid, breath, saliva, fingerprint;
  General or personal environment;
  Single or multiple measurands.

Other possible applications are:

Specific diagnostic configurations for detection of Bovine TB;

Specific diagnostic configurations for detection of Human TB at ports of entry;

The use of a series of aptamer sensors in parallel to detect a "biosignature" for TB quantitatively;

Specific biomarker—diagnostic configurations for detection of other diseases (e.g. Hepatitis B and C);

Specific diagnostic configurations for detection of biological warfare agents;

Specific diagnostic configurations for detection of explosives;

Specific diagnostic configurations for detection of drugs;

Specific diagnostic configurations for detection of noxious gases

The invention claimed is:

1. A device for identifying the presence of a specific target molecule or biomarker by the detection of a change in an electrical property, the device including a measurement sensor comprising:
a conducting or semiconducting sensor structure comprising a coating of aptamers or antibodies capable of conjugating with the target molecule or biomarker, thus giving rise to the said change in electrical property, and
an electrode system for conducting a signal from the device;
in which the device further includes a reference sensor, of substantially identical form but having the aptamers or antibodies of its sensor structure capped so as not to conjugate with the target molecule or biomarker, in order to act as an internal reference.

2. A device according to claim 1, in which the capping is effected by pre-saturation of the reference sensor structure with the target molecule or biomarker.

3. A device according to claim 1, in which the reference sensor structure contains an oligonucleotide aptamer and capping is effected by the sensor structure being bound to a complement oligonucleotide.

4. A device according to claim 1, in which the capping is effected by using a mutant version of the aptamer with sequence variations, such that the target molecule or biomarker is no longer recognized.

5. A device according to claim 1, in which the measurement and reference sensor structure are made on a semiconductor base coated with aptamers capable of conjugating with the target molecule or biomarker.

6. A device according to claim 5, in which the aptamers are stereospecific.

7. A device according to claim 5, the semiconductor base includes a Carbon Nanotube (CNT) backbone.

8. A device according to claim 7, in which a DNA strand is attached to the CNT backbone, with conjugation molecules attached to the DNA.

9. A device according to claim 5, in which the semiconductor base is a DNA backbone coated by a material selected from the group consisting of polyvinylpyrrolidone (PVP), aluminum (Al) and silicon (Si) to form a nanowire to give enhanced measurement of electrical properties.

10. A device according to claim 7, in which the electrode system includes a pair of interdigitated electrodes between which the measurement and reference sensor structure extends.

11. A device according to claim 10, in which the electrodes include conducting strips including an electrically-conductive material with a spacing larger than an average length of the CNTs.

12. A device according to claim 11, in which the conducting strips are spaced about 10-50 μm apart.

13. A device according to claim 1, further including a substrate on which the sensors and electrode system are formed.

14. A device according to claim 13, in which the substrate is a polymer selected from the group consisting of polyethylene terephthalate (PET), polyethylene naphthalate (PEN), polyvinylpyrrolidone (PVP) and polyethylene glycol (PEG).

15. A device according to claim 13, in which the substrate is silicon.

16. A device according to claim 1 and having two or more of the measurement sensors, each for a different target molecule or biomarker.

17. A device according to claim 1 and having one or more of the reference sensors and a plurality of the measurement sensors for multiple measurements of the same target molecule or biomarker.

18. A device according to claim 17, in which the measurement sensors are on the same substrate.

19. A device according to claim 16, where a ratio of the electrical properties measured from the measurement sensor and the reference sensor is used to identify the target molecule or biomarker.

20. A device according to claim 1, in which the electrical property measured is selected from the group consisting of resistance, conductance, capacitance, impedance, inductance and combinations thereof and is measured using DC or a high-frequency AC signal.

21. A device according to claim 5, in which the aptamers are associated with target molecules or biomarkers generated by a disease process.

22. A device according to claim 1, wherein the device is incorporated into a body moulding with appropriate electrical connections, the body moulding being sealed before use in an air-tight manner with a polymer barrier film.

23. A device according to claim 22, further including an interface between the electrodes and a reader device, the reader device measuring the response of the measurement sensor to provide a judgment or diagnosis.

24. A device according to claim 1, further including circuitry connected to the electrode system and adapted to compare the signals from the measurement sensor and the reference sensor to give a measurement of a concentration of the target molecule or biomarker in a sample.

25. A device according to claim 24, in which the device at a point of use checks the adequacy of a sample volume including the target molecule or biomarker via measurement of electrolyte in the sample volume before conjugation with the measurement sensor.

26. A device according to claim 1, further including software for the automated collection and dissemination of data from the device.

27. A device according to claim 1, wherein the aptamers are selected from the group consisting of deoxyribonucleic acid (DNA) aptamers, ribonucleic acid (RNA) aptamers, and peptide aptamers.

* * * * *